United States Patent
Grushin et al.

(10) Patent No.: US 6,919,139 B2
(45) Date of Patent: Jul. 19, 2005

(54) ELECTROLUMINESCENT IRIDIUM COMPOUNDS WITH PHOSPHINOALKOXIDES AND PHENYLPYRIDINES OR PHENYLPYRIMIDINES AND DEVICES MADE WITH SUCH COMPOUNDS

(75) Inventors: Vladimir Grushin, Hockessin, DE (US); Viacheslav A. Petrov, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 35 days.

(21) Appl. No.: 10/356,813

(22) Filed: Feb. 3, 2003

(65) Prior Publication Data

US 2003/0173896 A1 Sep. 18, 2003

Related U.S. Application Data

(60) Provisional application No. 60/356,886, filed on Feb. 14, 2002.

(51) Int. Cl.[7] .......................... H05B 33/12; C09K 11/06
(52) U.S. Cl. ...................... 428/690; 428/917; 313/506; 257/40; 257/98; 252/301.16; 544/225; 546/4
(58) Field of Search ................................ 428/690, 917; 313/504, 506; 252/301.16; 544/225; 546/4; 438/82; 251/98; 257/40

(56) References Cited

U.S. PATENT DOCUMENTS

| | | | |
|---|---|---|---|
| 6,670,645 B2 * | 12/2003 | Grushin et al. ............... | 257/98 |
| 2001/0019782 A1 | 9/2001 | Igarashi et al. | |
| 2002/0048689 A1 * | 4/2002 | Igarashi et al. ............. | 428/690 |
| 2003/0197183 A1 * | 10/2003 | Grushin et al. ............... | 257/79 |

FOREIGN PATENT DOCUMENTS

| | | |
|---|---|---|
| WO | WO 00/70655 A2 | 11/2000 |
| WO | WO 01/41512 A1 | 6/2001 |
| WO | WO 02/02714 A2 | 1/2002 |

OTHER PUBLICATIONS

Grushin, Vladimir V. et al., New efficient electroluminescent materials based on organometallic Ir complexes, Chem. Commun., 2001, 1494–1495.

Marsi, Kenneth L. et al., Synthesis, Structure Analysis, and Stereochemistry of Some Reactions of cis–and trans–2,2, 5–Trimethyl–3–phenyl–1,3–oxaphospholane, J. Org. Chem., 1977, 778–781.

Boere, Rene T. et al., Complexes of Hybrid Ligands, Synthesis of a Fluoro–Alcohol Diarylphosphino Ligand and Its Complexes with Pt2+, Pd2+, Ni2+, Co2+, Cu+, and Rh3+; Crystal and Molecular Structure of a Trans Square–Planar Ni2+ Complex with two Bidentate Ligands. Showing Cis–Trans Isomerism in Solution, Inorg. Chem. 1985, 3680–3687, 24, American Chemical Society.

Grushin, Vladimir V. et al., Facile preparation and synthetic applications of LI2CH2,C(CF3)2OKi, Journal of Fluorine Chemistry, 2002, 121–129, Elsevier Science B.V.

Baldo, M.A. et al., Very high–efficiency green organic light–emitting devices based on electrophosphorescence, Applied Physics Letters, Jul. 5, 1999, 4–6, vol. 75, No. 1, American Institute of Physics.

Barluenga, Jose et al., B–Substituted Organolithium Compounds from Chlorohydrins: Application to the Direct Synthesis of Bifunctional Organic Compounds, J. Chem. Soc. Perkin Trans. 1, 1983, 3019–3026.

* cited by examiner

Primary Examiner—Rena Dye
Assistant Examiner—Camie Thompson

(57) ABSTRACT

The present invention is generally directed to electroluminescent Ir(III) compounds with phosphinoalkoxides and phenylpyridines or phenylpyrimidines, and devices that are made with the Ir(III) compounds.

5 Claims, 3 Drawing Sheets (II)

(II-H)

(II)

(II-H)

(III)

(III-H)

(IV)

(V)

ELECTROLUMINESCENT IRIDIUM COMPOUNDS WITH PHOSPHINOALKOXIDES AND PHENYLPYRIDINES OR PHENYLPYRIMIDINES AND DEVICES MADE WITH SUCH COMPOUNDS

BACKGROUND OF THE INVENTION

1. Field of the Invention

This invention relates to electroluminescent complexes of iridium(III) with phenylpyridines or phenylpyrimidines, which additionally have a phosphinoalkoxide ligand. It also relates to electronic devices in which the active layer includes an electroluminescent Ir(III) complex.

2. Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, Friend et al., U.S. Pat. No. 5,247,190, Heeger et al., U.S. Pat. No. 5,408,109, and Nakano et al., Published European Patent Application 443 861. Complexes of 8-hydroxyquinolate with trivalent metal ions, particularly aluminum, have been extensively used as electroluminescent components, as has been disclosed in, for example, Tang et al., U.S. Pat. No. 5,552,678.

Burrows and Thompson have reported that fac-tris(2-phenylpyridine) iridium can be used as the active component in organic light-emitting devices. (*Appl. Phys. Lett.* 1999, 75, 4.) The performance is maximized when the iridium compound is present in a host conductive material. Thompson has further reported devices in which the active layer is poly(N-vinyl carbazole) doped with fac-tris[2-(4',5'-difluorophenyl)pyridine-$C^{'2}$,N]iridium(III). (Polymer Preprints 2000, 41(1), 770.) Additional electroluminescent devices with an active layer of polymer doped with organometallic complexes of iridium have been described by Burrows and Thompson in published PCT applications WO 00/70655 and WO 01/41512. Most of these complexes have emission spectra with peaks in the green or blue-green region.

However, there is a continuing need for electroluminescent compounds having improved efficiency and/or having emission maxima in the blue region of the spectrum.

SUMMARY OF THE INVENTION

The present invention is directed to an iridium compound having the following Formula I:

$$IrL^aL^bL' \qquad (I)$$

where $L^a$ and $L^b$ are alike or different and each of $L^a$ and $L^b$ has Formula II, shown in FIG. 1, wherein:

$R^1$ through $R^8$ are independently selected from hydrogen, deuterium, alkyl, alkoxy, halogen, nitro, cyano, fluoro, $C_n(H+F)_{2n+1}$, $OC_n(H+F)_{2n+1}$, and $OCF_2X$, where n is an integer from 1 through 12, and X is H, Cl, or Br, and A is C or N, provided that when A is N, there is no $R^1$; and L' is a bidentate phosphino alkoxide ligand having Formula III, shown in FIG. 2, wherein:

$R^9$ can be the same or different at each occurrence and is selected from $C_m(H+F)_{2n+1}$, $C_6(H+F)_pY_{5-p}$, $R^{10}$ can be the same or different at each occurrence and is selected from H, F, and $C_n(H+F)_{2n+1}$;

Y is $C_m(H+F)_{2m+1}$;

n is an integer from 1 through 12;

m is 2 or 3;

p is 0 or an integer from 1 through 5.

In another embodiment, the present invention is directed to phosphinoalkanol precursor compounds from which the phosphinoalkoxide ligands are made. The phosphinoalkanol compounds have Formula III-H, shown in FIG. 2, in which $R^9$, $R^{10}$, Y, n, m, and p are as defined above for Formula III.

In another embodiment, the present invention is directed to a process for making a phosphinoalkanolcompound.

In another embodiment, the present invention is directed to an organic electronic device having at least one emitting layer comprising the above Ir(III) compound, or combinations of the above Ir(III) compounds.

As used herein, the term "compound" is intended to mean an electrically uncharged substance made up of molecules that further consist of atoms, wherein the atoms cannot be separated by physical means. The term "ligand" is intended to mean a molecule, ion, or atom that is attached to the coordination sphere of a metallic ion. The term "complex", when used as a noun, is intended to mean a compound having at least one metallic ion and at least one ligand. The term "group" is intended to mean a part of a compound, such a substituent in an organic compound or a ligand in a complex. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "photoactive" refers to any material that exhibits electroluminescence and/or photosensitivity. The term "(H+F)" is intended to mean all combinations of hydrogen and fluorine, including completely hydrogenated, partially fluorinated or perfluorinated substituents. By "emission maximum" is meant the wavelength, in nanometers, at which the maximum intensity of electroluminescence is obtained. Electroluminescence is generally measured in a diode structure, in which the material to be tested is sandwiched between two electrical contact layers and a voltage is applied. The light intensity and wavelength can be measured, for example, by a photodiode and a spectrograph, respectively. In addition, the IUPAC numbering system is used throughout, where the groups from the Periodic Table are numbered from left to right as 1 through 18 (CRC Handbook of Chemistry and Physics, 81$^{st}$ Edition, 2000).

DETAILED DESCRIPTION OF THE PREFERRED EMBODIMENTS

The Ir(III) compounds of the invention have Formula I, as defined above. The compounds are frequently referred to as bis-cyclometalated complexes. The cyclometalated complexes of the invention are neutral and non-ionic, and can be sublimed intact. Thin films of these materials obtained via vacuum deposition exhibit good to excellent electroluminescent properties.

Figure 1A:
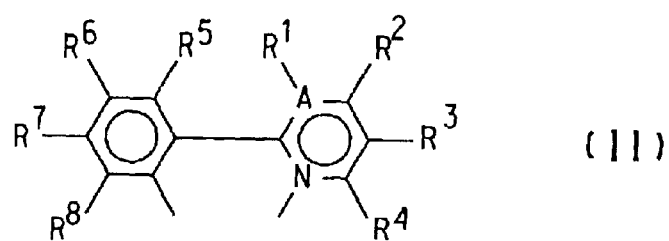
FIG. 1 shows Formula II for phenylpyridine and phenylpyrimidine ligands useful in the metal complex of the invention, and Formula II-H for the ligand precursor compound.
Figure 1B:
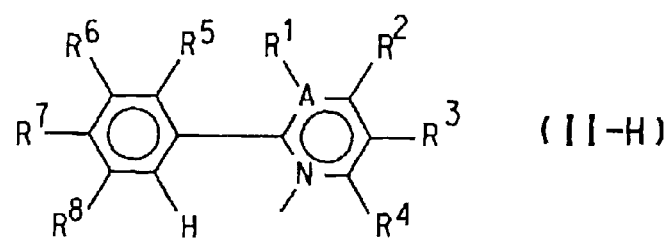

Two of the ligands in the Ir(III) compounds of the invention, are phenylpyridine or phenylpyrimidine ligands having Formula II, shown in FIG. 1. The $R^1$ through $R^8$ groups of Formula II may be chosen from conventional substitutents for organic compounds, such as alkyl, alkoxy, halogen, nitro, and cyano groups, as well as fluoro, fluorinated alkyl and fluorinated alkoxy groups. The groups can be partially or fully fluorinated (perfluorinated).

Figure 3:
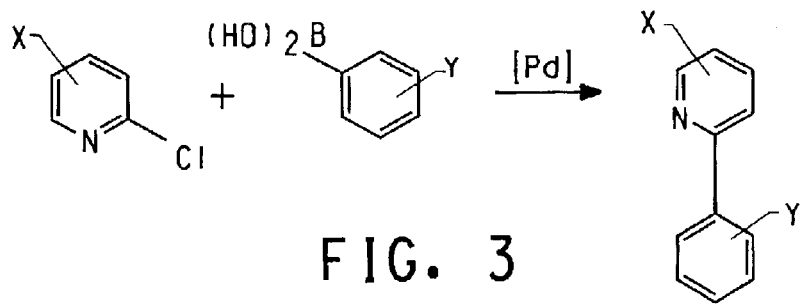
FIG. 3 shows Equation 1 for forming the ligand precursor compound, II-H.

The precursor 2-phenylpyridines and 2-phenylpyrimidines, Formula II-H in FIG. 1, are prepared, in good to excellent yield, using the Suzuki coupling of the substituted 2-chloropyridine or 2-chloropyrimidine with arylboronic acid as described in O. Lohse, P. Thevenin, E. Waldvogel *Synlett*, 1999, 45–48. This reaction is illustrated for the pyridine derivative, where X and Y represent substituents, in Equation (1) shown in FIG. 3.

Examples of 2-phenylpyridine and 2-phenylpyrimidine compounds, having Formula II-H, are given in Table 1 below:

TABLE 1

| Compound | A | $R_1$ | $R_2$ | $R_3$ | $R_4$ | $R_5$ | $R_6$ | $R_7$ | $R_8$ | $R_9$ |
|---|---|---|---|---|---|---|---|---|---|---|
| 1-a | C | H | H | $CF_3$ | H | F | H | H | H | H |
| 1-b | C | H | H | $CF_3$ | H | H | $CF_3$ | H | H | H |
| 1-c | C | H | H | $NO_2$ | H | H | $CF_3$ | H | H | H |
| 1-d | C | H | H | $CF_3$ | H | H | F | H | H | H |
| 1-e | C | H | H | $CF_3$ | H | H | H | $CH_3O$ | H | H |
| 1-f | C | Cl | H | $CF_3$ | H | H | H | H | H | H |
| 1-g | C | H | H | H | $CH_3$ | H | H | F | H | H |
| 1-h | N | — | H | H | H | H | H | F | H | H |
| 1-i | C | H | H | $CF_3$ | H | H | H | $CF_3O$ | H | H |
| 1-j | N | — | $CF_3$ | H | H | F | H | H | H | H |
| 1-k | C | H | H | $CF_3$ | H | H | H | F | H | H |
| 1-l | C | $CF_3$ | H | H | H | H | H | H | H | H |
| 1-m | C | Cl | H | $CF_3$ | H | H | H | F | H | H |
| 1-n | C | $CF_3$ | H | H | H | H | H | F | H | H |
| 1-o | C | $CF_3$ | H | H | H | H | H | $CH_3O$ | H | H |
| 1-p | C | Cl | H | $CF_3$ | H | H | H | $CH_3O$ | H | H |
| 1-q | N | — | $CF_3$ | H | H | H | H | F | H | H |
| 1-r | C | Cl | H | $CF_3$ | H | H | H | H | H | H |
| 1-s | C | H | H | $CF_3$ | H | H | H | H | H | H |
| 1-t | C | Cl | H | H | H | F | H | H | H | H |
| 1-v | C | H | H | $CF_3$ | H | H | $CH_3O$ | H | H | H |
| 1-w | C | H | $CH_3O$ | H | H | H | H | $CF_3$ | H | H |
| 1-x | C | H | H | H | H | H | F | F | H | H |
| 1-y | C | H | H | $CF_3$ | H | H | F | H | F | H |
| 1-z | C | H | H | $CF_3$ | H | F | H | F | H | H |
| 1-aa | C | H | H | Br | H | H | H | Br | H | H |
| 1-ab | C | H | $CH_3$ | H | H | F | H | F | H | H |
| 1-ac | C | H | $CH_3$ | H | H | H | $CF_3$ | H | $CF_3$ | H |
| 1-ad | C | H | H | $CH_3$ | H | F | H | F | H | H |
| 1-ae | C | H | $CH_3$ | H | H | H | $CF_3$ | H | H | H |
| 1-af | C | H | H | $CH_3$ | H | H | $CF_3$ | H | $CF_3$ | H |
| 1-ag | C | H | H | H | H | H | $CF_3$ | H | H | H |
| 1-ah | C | H | H | H | H | F | H | F | H | H |
| 1-ai | C | H | t-Bu | H | H | F | H | F | H | H |
| 1-aj | C | H | t-Bu | H | H | H | $CF_3$ | H | $CF_3$ | H |
| 1-ak | C | H | $CH_3$ | H | H | H | H | $CF_3$ | H | H |
| 1-al | C | H | H | H | H | $CH_3O$ | H | $CH_3O$ | H | H | where "t-Bu" represents a tertiary butyl group.

Figure 2A:
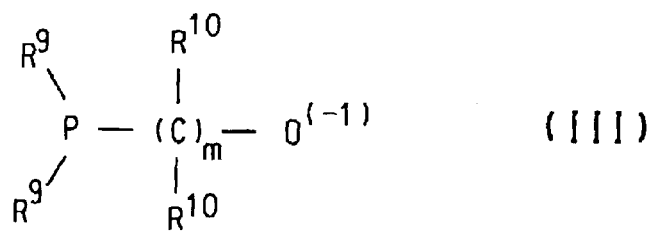
FIG. 2 shows Formula III for phosphinoalkanoxide ligands useful in the metal complex of the invention, and Formula III-H for the ligand precursor compound.
Figure 2B:
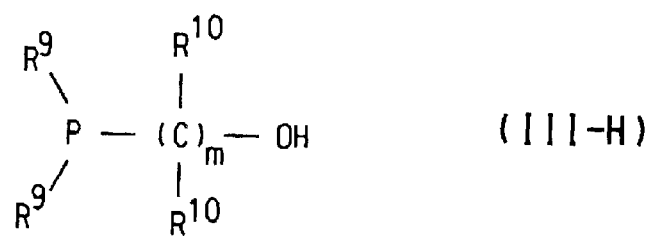

The third ligand in the Ir(III) compounds of the invention is a phosphinoalkoxide. The precursor phosphinoalkanol compounds having Formula III-H, as shown in FIG. 2, can be prepared using known procedures, such as, for example, the procedure reported in *Inorg. Chem.* 1985, v. 24, p. 3680, for 1,1-bis(trifluoromethyl)-2-(diphenylphosphino)ethanol. This method involves the reaction of diphenylphosphinomethyllithium with hexafluoroacetylacetone, followed by hydrolysis.

Alternatively, the phosphino alkanol compounds can be prepared using the reaction of 1,1-bis(trifluoromethyl) ethylene oxide with the corresponding secondary phosphine ($R^9_2PH$) or its deprotonated form as a salt ($[R^9_2P]M$), where M is Li, Na, or K. The deprotonated form can be prepared by the treatment of the secondary phosphine with a strong base, such as BuLi or t-BuOK.

Alternatively, the phosphino alkanol compounds can be made using dilithiated derivatives of halohydrins, which can be prepared as described in *J. Chem. Soc., Perkin Trans.* 1, 1983, p. 3019. The dilithio-derivative is reacted with a chlorophosphine to produce the desired phosphinoalkanol ligand. Halohydrins are made by a variety of literature methods, such as ring-opening of an epoxide (also called an "oxirane") with HHal (Hal=Cl, Br, I; see: *J. Am. Chem. Soc.* 1960, vol. 82, p. 2288). This is particularly useful for 1,1-bis(trifluoromethyl)ethylene oxide which can be prepared as described in Petrov, V. A. et al., WO 00/66575, PCT/US0011746, Chem. Abstr. 2000, 350691. In the process of the invention, a dried bromohydrin is combined with n-butyl lithium, wherein the molar ratio of n-butyl lithium to bromohydrin is about 2. The preferred process for preparing the phosphino alkanol comprises the steps:

(1) combining an epoxide with aqueous HBr, to form a bromohydrin;

(2) isolating the bromohydrin from step (1) and removing water;

(3) combining the dried bromohydrin from step (2) with n-butyl lithium, wherein the molar ratio of n-butyl lithium to the bromohydrin is about 2;

(4) adding a chlorophosphine to the product of step (3); and (5) adding acid to the product of step (4).

Figure 4:
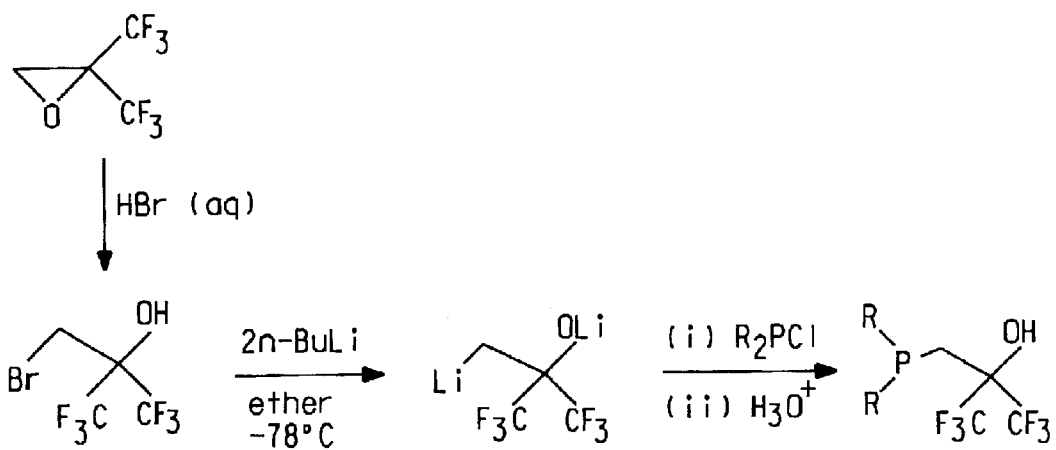
FIG. 4 shows Equation 2 for forming the ligand precursor compound, III-H.

The epoxide can be substituted with groups such as alkyl, partially fluorinated alkyl, and perfluoroalkyl groups; preferably trifluoromethyl groups. The chlorophosphine is a chlorodialkylphosphine or a chlorodiarylphosphine; preferably, chlorodiphenylphosphine. The acid can be any Bronsted acid which will provide a proton in the last reaction step, preferably trifluoroacetic acid. The reaction scheme is illustrated using bis(trifluoromethyl)ethylene oxide in Equation (2), shown in FIG. 4. The dilithiation of the bromohydrin deriving from bis(trifluoromethyl)ethylene oxide can be done with 2 equivalents of BuLi within 0.5 h at −78° C. This is different from the literature procedure (*J. Chem. Soc., Perkin Trans.* 1, 1983, p. 3019) which employs 1 equivalent of BuLi for 3 hours, followed by 1 equivalent of naphthyl lithium for 5 hours at −78° C. Napthyl lithium is not commercially available and is more expensive to make. The process of the invention is, in general, faster and uses readily available butyl lithium.

In the preferred phosphinoalkanol of Formula III-H, $R^9$ is $C_6F_5$ or $C_6H_pY_{5-p}$, where Y is $CF_3$ and p is 3 or 4. Preferably at least one of $R^{10}$ is $CF_3$ and m is 2.

Examples of suitable phosphinoalkanol compounds, with the abbreviation in brackets, include:

1-diphenylphosphino-2-propanol [dppOH]

1-bis(trifluoromethyl)-2-(diphenylphosphino)ethanol [PO-1H]

1,1-bis(trifluoromethyl)-2-(bis(3'5'-ditrifluoromethylphenyl)phosphino)ethanol [PO-2H]

1,1-bis(trifluoromethyl)-2-(bis(4'-trifluoromethylphenyl)phosphino)ethanol [PO-3H]

1,1-bis(trifluoromethyl)-2-(bis(pentafluorophenyl)phosphino)ethanol [PO-4H]

The phosphinoalkoxide ligands from the above compounds are, respectively (abbreviations provided in brackets):

1-diphenylphosphino-2-propoxide [dppO]

1-bis(trifluoromethyl)-2-(diphenylphosphino)ethoxide [PO-1]

1,1-bis(trifluoromethyl)-2-(bis(3'5'-ditrifluoromethylphenyl)phosphino)ethoxide [PO-2]

1,1-bis(trifluoromethyl)-2-(bis(4'-trifluoromethylphenyl)phosphino)ethoxide [PO-3]

1,1-bis(trifluoromethyl)-2-(bis(pentafluorophenyl)phosphino)ethoxide [PO-4]

Figure 5A:
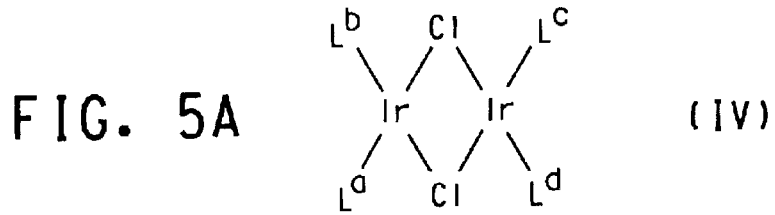
FIG. 5 shows Formulae IV and V for bridged Ir dimers.
Figure 5B:
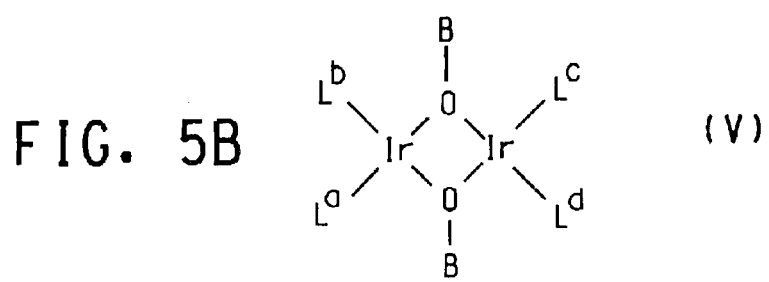
Figure 6:
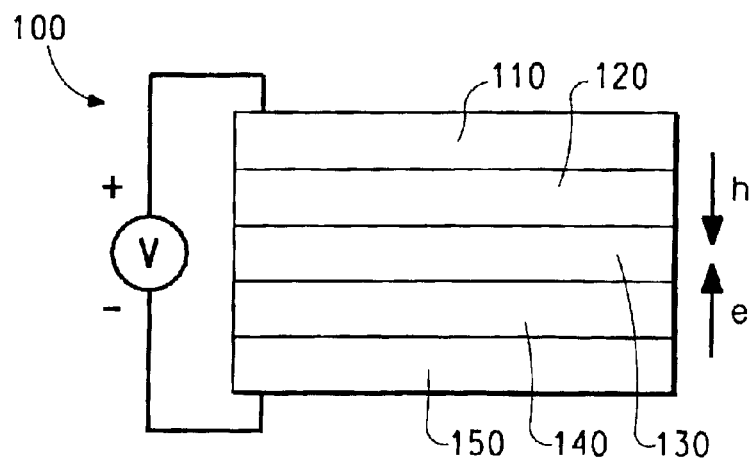
FIG. 6 is a schematic diagram of a light-emitting device (LED).

The iridium complexes of the invention can be prepared by first preparing an intermediate iridium dimer with the phenylpyridine or phenypyrimidine ligand. The dimer can be the dichloro bridged dimer having Formula IV, shown in FIG. 5, or the dihydroxo bridged dimer having Formula V, shown in FIG. 5, where:

in Formulae IV and V:

$L^a$, $L^b$, $L^c$, and $L^d$ can be the same or different from each other and each of $L^a$, $L^b$, $L^c$, and $L^d$ has Formula II, as defined above;

in Formula V:

B=H, $CH_3$, or $C_2H_5$.

The dichloro bridged dimers having Formula IV, can generally be prepared by reacting iridium trichloride hydrate with the 2-phenylpyridine or 2-phenylpyrimidine in a suitable solvent, such as 2-ethoxyethanol. The iridium bridged dimers having Formula V, can generally be prepared by reacting iridium trichloride hydrate with the 2-phenylpyridine or 2-phenylpyrimidine, and then adding NaOB. These dicyclometalated complexes can be isolated and (optionally) purified before the reaction with the phosphinoalkanols or used without isolation, as described in the examples below. The chloro dicyclometalated complexes can react, under biphasic or homogeneous conditions, with either the phosphinoalkanols in the presence of a base, such as NaOH, or salts of the phosphinoalkanols. When salts of the phosphinoalkanols are used with the dichloro bridged dimers, and also when intermediates having Formula V are used, no additional base is required for the synthesis.

Examples of compounds having Formula I, where $L^a$ is the same as $L^b$, are given in Table 2 below, where $R^1$ through $R^8$ are as shown in Formula I, and A is C.

TABLE 2

| Comp. | L' | $R^1$ | $R^2$ | $R^3$ | $R^4$ | $R^5$ | $R^6$ | $R^7$ | $R^8$ |
|---|---|---|---|---|---|---|---|---|---|
| 2-a | PO-1 | H | $CH_3$ | H | H | F | H | F | H |
| 2-b | PO-2 | H | $CH_3$ | H | H | F | H | F | H |
| 2-c | PO-1 | H | H | H | H | F | H | F | H |

TABLE 2-continued

| Comp. | L' | R$^1$ | R$^2$ | R$^3$ | R$^4$ | R$^5$ | R$^6$ | R$^7$ | R$^8$ |
|---|---|---|---|---|---|---|---|---|---|
| 2-d | PO-2 | H | H | H | H | F | H | F | H |
| 2-e | PO-1 | H | H | H | H | H | CF$_3$ | H | H |
| 2-f | PO-1 | H | CH$_3$ | H | H | H | CF$_3$ | H | CF$_3$ |
| 2-g | PO-2 | H | CH$_3$ | H | H | H | CF$_3$ | H | CF$_3$ |
| 2-h | PO-1 | H | H | CH$_3$ | H | F | H | F | H |
| 2-i | PO-2 | H | H | CH$_3$ | H | F | H | F | H |
| 2-j | PO-1 | H | H | CF$_3$ | H | H | H | F | H |
| 2-k | PO-1 | H | t-Bu | H | H | F | H | F | H |
| 2-l | PO-1 | H | t-Bu | H | H | H | CF$_3$ | H | CF$_3$ |
| 2-m | PO-3 | H | H | CH$_3$ | H | F | H | F | H |
| 2-n | PO-3 | H | CH$_3$ | H | H | F | H | F | H |
| 2-o | PO-1 | H | H | H | H | CH$_3$O | H | CH$_3$O | H |
| 2-p | PO-2 | H | H | H | H | CH$_3$O | H | CH$_3$O | H |
| 2-q | PO-1 | H | CH$_3$ | H | H | H | CF$_3$ | H | H |
| 2-r | PO-2 | H | CH$_3$ | H | H | H | CF$_3$ | H | H |
| 2-s | PO-1 | H | CH$_3$ | H | H | H | H | CF$_3$ | H |
| 2-t | PO-4 | H | CH$_3$ | H | H | H | CF$_3$ | H | CF$_3$ |
| 2-u | PO-4 | H | CH$_3$ | H | H | F | H | F | H |
| 2-v | PO-2 | H | H | H | H | H | H | H | H | where "t-Bu" represents a tertiary butyl group.

Electronic Device

The present invention also relates to an electronic device comprising at least one photoactive layer positioned between two electrical contact layers, wherein the at least one layer of the device includes the iridium complex of the invention. Devices frequently have additional hole transport and electron transport layers. A typical structure is shown in FIG. 1. The device 100 has an anode layer 110 and a cathode layer 150. Adjacent to the anode is a layer 120 comprising hole transport material. Adjacent to the cathode is a layer 140 comprising an electron transport material. Between the hole transport layer and the electron transport layer is the photoactive layer 130. Layers 120, 130, and 140 are individually and collectively referred to as the active layers.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are describe in Markus, John, *Electronics and Nucleonics Dictionary*, 470 and 476 (McGraw-Hill, Inc. 1966).

The iridium compounds of the invention are particularly useful as the photoactive material in layer 130, or as electron transport material in layer 140. Preferably the iridium complexes of the invention are used as the light-emitting material in diodes. It has been found that in these applications, the compounds of the invention do not need to be in a solid matrix diluent in order to be effective. A layer that is greater than 20% by weight iridium compound, based on the total weight of the layer, up to 100% iridium compound, can be used as the emitting layer. Additional materials can be present in the emitting layer with the iridium compound. For example, a fluorescent dye may be present to alter the color of emission. A diluent may also be added. The diluent can be a polymeric material, such as poly(N-vinyl carbazole) and polysilane. It can also be a small molecule, such as 4,4'-N,N'-dicarbazole biphenyl or tertiary aromatic amines. When a diluent is used, the iridium compound is generally present in a small amount, usually less than 20% by weight, preferably less than 10% by weight, based on the total weight of the layer.

In some cases the iridium complexes may be present in more than one isomeric form, or mixtures of different complexes may be present. It will be understood that in the above discussion of OLEDs, the term "the iridium compound" is intended to encompass mixtures of compounds and/or isomers.

To achieve a high efficiency LED, the HOMO (highest occupied molecular orbital) of the hole transport material should align with the work function of the anode, the LUMO (lowest un-occupied molecular orbital) of the electron transport material should align with the work function of the cathode. Chemical compatibility and sublimation temp of the materials are also important considerations in selecting the electron and hole transport materials.

The other layers in the OLED can be made of any materials which are known to be useful in such layers. The anode 110, is an electrode that is particularly efficient for injecting positive charge carriers. It can be made of, for example materials containing a metal, mixed metal, alloy, metal oxide or mixed-metal oxide, or it can be a conducting polymer. Suitable metals include the Group 11 metals, the metals in Groups 4, 5, and 6, and the Group 8–10 transition metals. If the anode is to be light-transmitting, mixed-metal oxides of Groups 12, 13 and 14 metals, such as indium-tin-oxide, are generally used. The anode 110 may also comprise an organic material such as polyaniline as described in "Flexible light-emitting diodes made from soluble conducting polymer," *Nature* vol. 357, pp 477–479 (11 Jun. 1992). At least one of the anode and cathode should be at least partially transparent to allow the generated light to be observed.

Examples of hole transport materials for layer 120 have been summarized for example, in Kirk-Othmer Encyclopedia of Chemical Technology, Fourth Edition, Vol. 18, p. 837–860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine ("TPD"), 1,1-bis[(di-4-tolylamino)phenyl]cyclohexane ("TAPC"), N,N'-bis(4-methylphenyl)-N,N'-bis(4-ethylphenyl)-[1,1'-(3,3'-dimethyl)biphenyl]-4,4'-diamine ("ETPD"), tetrakis-(3-methylphenyl)-N,N,N', N'-2,5-phenylenediamine ("PDA"), a-phenyl-4-N,N-diphenylaminostyrene ("TPS"), p-(diethylamino)-benzaldehyde diphenylhydrazone ("DEH"), triphenylamine ("TPA"), bis[4-(N,N-diethylamino)-2-methylphenyl](4-methylphenyl)methane ("MPMP"), 1-phenyl-3-[p-(diethylamino)styryl]-5-[p-(diethylamino)phenyl]pyrazoline ("PPR" or "DEASP"), 1,2-trans-bis(9H-carbazol-9-yl)cyclobutane ("DCZB"), N,N,N',N'-tetrakis(4-methylphenyl)-(1,1'-biphenyl)-4,4'-diamine ("TTB"), and porphyrinic compounds, such as copper phthalocyanine. Commonly used hole transporting polymers are polyvinylcarbazole, (phenylmethyl)polysilane, and polyaniline. It is also possible to obtain hole transporting polymers by doping hole transporting molecules such as those mentioned above into polymers such as polystyrene and polycarbonate.

Examples of electron transport materials for layer 140 include metal chelated oxinoid compounds, such as tris(8-hydroxyquinolato)aluminum ("Alq$_3$"); phenanthroline-based compounds, such as 2,9-dimethyl-4,7-diphenyl-1,10-phenanthroline ("DDPA") or 4,7-diphenyl-1,10-phenanthroline ("DPA"), and azole compounds such as 2-(4-biphenylyl)-5-(4-t-butylphenyl)-1,3,4-oxadiazole ("PBD") and 3-(4-biphenylyl)-4-phenyl-5-(4-t-butylphenyl)-1,2,4-triazole ("TAZ"). Layer 140 can function both to facilitate electron transport, and also serve as a buffer layer or confinement layer to prevent quenching of the exciton at layer interfaces. Preferably, this layer promotes electron mobility and reduces exciton quenching.

The cathode 150, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds can also be deposited between the organic layer and the cathode layer to lower the operating voltage.

It is known to have other layers in organic electronic devices. For example, there can be a layer (not shown) between the conductive polymer layer 120 and the active layer 130 to facilitate positive charge transport and/or band-gap matching of the layers, or to function as a protective layer. Similarly, there can be additional layers (not shown) between the active layer 130 and the cathode layer 150 to facilitate negative charge transport and/or band-gap matching between the layers, or to function as a protective layer. Layers that are known in the art can be used. In addition, any of the above-described layers can be made of two or more layers. Alternatively, some or all of inorganic anode layer 110, the conductive polymer layer 120, the active layer 130, and cathode layer 150, may be surface treated to increase charge carrier transport efficiency. The choice of materials for each of the component layers is preferably determined by balancing the goals of providing a device with high device efficiency.

It is understood that each functional layer may be made up of more than one layer.

The device can be prepared by sequentially vapor depositing the individual layers on a suitable substrate. Substrates such as glass and polymeric films can be used. Conventional vapor deposition techniques can be used, such as thermal evaporation, chemical vapor deposition, and the like. Alternatively, the organic layers can be coated from solutions or dispersions in suitable solvents, using any conventional coating technique. In general, the different layers will have the following range of thicknesses: anode 110, 500–5000 Å, preferably 1000–2000 Å; hole transport layer 120, 50–1000 Å, preferably 200–800 Å; light-emitting layer 130, 10–1000 Å, preferably 100–800 Å; electron transport layer 140, 50–1000 Å, preferably 200–800 Å; cathode 150, 200–10000 Å, preferably 300–5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

It is understood that the efficiency of devices made with the iridium compounds of the invention, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

The iridium complexes of the invention are phosphorescent and photoluminescent and may be useful in applications other than OLEDs. For example, organometallic complexes of iridium have been used as oxygen sensitive indicators, as phosphorescent indicators in bioassays, and as catalysts.

EXAMPLES

The following examples illustrate certain features and advantages of the present invention. They are intended to be illustrative of the invention, but not limiting. All percentages are by weight, unless otherwise indicated.

Example 1

This example illustrates the preparation of the 2-phenylpyridines and 2-phenylpyrimidines which are used to form the iridium compounds.

The general procedure used was described in O. Lohse, P. Thevenin, E. Waldvogel *Synlett*, 1999, 45–48. In a typical experiment, a mixture of 200 ml of degassed water, 20 g of potassium carbonate, 150 ml of 1,2-dimethoxyethane, 0.5 g of Pd(PPh$_3$)$_4$, 0.05 mol of a substituted 2-chloropyridine (quinoline or pyrimidine) and 0.05 mol of a substituted phenylboronic acid was refluxed (80–90° C.) for 16–30 h. The resulting reaction mixture was diluted with 300 ml of water and extracted with CH$_2$Cl$_2$ (2×100 ml). The combined organic layers were dried over MgSO$_4$, and the solvent removed by vacuum. The liquid products were purified by fractional vacuum distillation. The solid materials were recrystallized from hexane. The typical purity of isolated materials was >98%.

2-(2',4'-dimethoxyphenyl)pyridine was prepared via Kumada coupling of 2-chloropyridine with 2,4-dimethoxyphenylmagnesium bromide in the presence of [(dppb)PdCl$_2$] catalyst, where dppb represents 1,4-bis (diphenylphosphino)butane).

The starting materials, yields, melting and boiling points of the new materials are given in Table 3. NMR data and analytical data are given in Table 4.

TABLE 3

Preparation of 2-Phenyl Pyridines, Phenylpyrimidines and Phenylquinolines

| Compound | Yield in % | B.p./mm Hg (m.p.) in ° C. |
| --- | --- | --- |
| 1-s | 70 | — |
| 1-a | 72 | — |

TABLE 3-continued

Preparation of 2-Phenyl Pyridines, Phenylpyrimidines and Phenylquinolines

| Compound | Yield in % | B.p./mm Hg (m.p.) in °C. |
|---|---|---|
| 1-b | 48 | — |
| 1-u | 75 | (76–78) |
| 1-c | 41 | (95–96) |
| 1-d | 38 | (39–40) |
| 1-e | 55 | 74.5/0.1 |
| 1-g | 86 | 71–73/0.07 |
| 1-t | 65 | 77–78/0.046 |
| 1-k | 50 | (38–40) |
| 1-m | 80 | 72–73/0.01 |
| 1-f | 22 | 52–33/0.12 |
| 1-v | 63 | 95–96/13 |
| 1-w | 72 | |
| 1-x | 35 | 61–62/0.095 |
| 1-y | 62 | (68–70) |
| 1-z | 42 | 66–67/0.06 (58–60) |
| 1-aa | 60 | |
| 1-ab | 61.5 | 70–72/0.03 |
| 1-ac | 39 | 66–68/0.01 |
| 1-ad | 76 | 75–76/0.01 (54–56) |
| 1-ae | 76 | 69–70/0.06 (44–46) |
| 1-af | 84 | (83–85) |
| 1-ag | 72 | 64–65/0.026 |
| 1-ah | 36 | 62/0.01 |
| 1-ai | 49 | 99–101/0.26 |
| 1-aj | 58 | 108–109/0.1 |
| 1-ak | 46 | 76–77/01 (52–54) |

TABLE 4

Properties of 2-Phenyl Pyridines, Phenylpyrimidines and Phenylquinolines

| Compound | ¹H NMR | ¹⁹F NMR | Analysis %, found (calc.) or MS (M⁺) |
|---|---|---|---|
| 1-s | 7.48(3H), 7.70(1H), 7.83(1H), 7.90(2H), 8.75(1H) | −62.68 | C, 64.50 (64.57) H, 3.49 (3.59) N, 6.07 (6.28) |
| 1-a | 7.19(1H), 7.30(1H), 7.43(1H), 7.98(2H), 8.07(1H) 9.00(1H) | −60.82 (3F, s), −116.96 (1F, m) | C, 59.56 (59.75) H, 3.19 (2.90) N, 5.52 (5.81) |
| 1-b | 7.58(1H), 7.66(1H), 7.88(1H), 8.03(1H), 8.23(1H), 8.35(1H) 8.99(1H) | −62.75 (3F, s), −63.10 (3F, s) | C, 53.68 (53.60) H, 2.61 (2.40) N, 4.53 (4.81) |
| 1-u | 7.55(1H), 7.63(1H), 7.75(2H), 7.89(2H), 8.28(2H), 8.38(1H), 8.50(1H) | −62.89 (s) | C, 69.17 (70.33) H, 3.79 (3.66) N, 4.88 (5.12) |
| 1-c | 7.53(1H), 7.64(1H), 7.90(1H), 8.18(1H), 8.30(1H), 8.53(1H), 9.43(1H) | −62.14 (s) | C, 53.83 (53.73) H, 2.89 (2.61) N, 9.99 (10.44) |
| 1-d | 7.06(1H), 7.48(1H), 7.81(3H), 8.01(1H), 8.95(1H), | −62.78 (3F, s), −112.61 (1F, m) | C, 59.73 (59.75) H, 2.86 (2.90) N, 5.70 (5.81) |
| 1-e | 3.80(3H) 6.93(2H), 7.68(1H), 7.85(1H), 7.96(2H), 8.82(1H) | −62.63 (s) | C, 61.66 (61.90) H, 3.95 (4.04) N, 5.53 (5.38) |
| 1-g | 2.70(3H) 7.10(3H), 7.48(1H), 7.60(1H), 8.05(2H), | −114.03 (m) | C, 76.56 (77.00) H, 5.12 (5.30) N, 5.43 (7.50) |
| 1-t | 7.10(2H), 7.35(2H), 7.96(1H), 8.78(1H) | −62.73 (3F, s), −113.67 (1F, m) | C, 50.51 (52.17) H, 1.97 (2.17) N, 5.09 (5.07) |
| 1-k | 7.08(2H), 7.62(1H), 7.90(3H), 8.80(1H) | −62.75 (3F, s), −111.49 (m) | C, 60.39 (59.75), H, 3.38 (2.90), N, 5.53 (5.51) |
| 1-m | 7.10(2H), 7.80(2H), 8.00(1H), 8.75(1H) | −62.63 (3F, s), −111.24 (m) | C, 52.13 (52.17) H, 2.16 (2.17) N, 4.85 (5.07) |
| 1-f | 7.55(3H), 7.77(2H), 8.06(1H), 8.87(1H) | −62.57 (s) | 257(M⁺, C₁₂H₇F₃ClN⁺), 222(M-Cl) |
| 1-v | 3.8(3H), 6.95(1H), 7.30(1H), 7.50(1H), 7.58(1H), 7.75(1H), 7.90(1H), 8.87(1H) | −62.70 ppm | C, 61.66 (61.37), H, 3.98 (3.67), N, 5.53 (5.48) |
| 1-w | 8.54(1H, d), 8.21 (2H, d), 7.70(2H, d), 7.24 (1H, s), 6.82(1H, dd), 3.91 (3H, s) | −63.08 (3F, s) | |
| 1-x | 6.9(2H, m), 7.18 (2H, m), 7.68(2H, m), 7.95(1H, m), 8.65(1H, m); | −109.70 (1F, m), −113.35 (1F, m). | |
| 1-y | 6.94(1H), 7.62(2H), 7.82(1H), 8.03(1H), 8.96(1H); | −62.72 (3F, s), −109.11 (2F, m) | |
| 1-z | 6.85(1H), 6.93(1H), 7.80, 7.90, | −62.80 (3F, s), −107.65 (1F, m), −112.45 (1F, m). | |

TABLE 4-continued

Properties of 2-Phenyl Pyridines, Phenylpyrimidines and Phenylquinolines

| Compound | $^1$H NMR | $^{19}$F NMR | Analysis %, found (calc.) or MS (M$^+$) |
|---|---|---|---|
| 1-aa | 8.05(3H), 8.89(1H); 7.70(3H, m), 7.85(3H, m), 7.80, 7.90, 8.85(1H, m). | | |
| 1-ab | 2.39(3H), 6.99(2H), 7.02(1H), 7.57(1H), 7.99(1H), 8.56(1H) | −102.96 (1F, m), −113.18 (1F, m) | |
| 1-ac | 2.47(3H), 7.17(1H), 7.63(1H), 7.91(1H), 8.48(2H), 8.60(1H), 9.00(1H) | −63.23 (s) | |
| 1-ad | 2.25(3H), 6.90(2H), 7.55(2H), 8.50(1H), 8.85(1H), | −110.37 (1F, m), −113.50 (1F, m) | |
| 1-ae | 2.35(3H), 7.05(1H), 7.55(2H), 8.01(1H), 8.18(1H), 8.50(1H) | −63.03 (s) | |
| 1-af | 2.43(3H) 7.66(1H), 7.87(1H), 8.47(2H), 8.59(1H) | −63.18 (s) | |
| 1-ag | 7.20(1H), 7.65(3H), 8.10(1H), 8.17(1H), 8.65(1H), 9.43(1H) | −63.05 (s) | |
| 1-ah | 6.90(1H), 7.18(2H), 7.68(2H), 7.95(1H), 8.65(1H), | −109.70 (1F, m), −113.35 (1F, m) | |
| 1-aj | 1.35(9H), 7.34(1H), 7.72(1H), 7.88(1H), 8.44(2H), 8.61(1H) | −63.19 | |
| 1-ak | 2.46(3H), 7.15(1H), 7.60(1H), 7.73(2H), 8.11(2H), 8.59(1H) | −62.86 | |

Compound 1-al has been reported previously in the literature.

Examples 2–4

These examples illustrate the preparation of the phosphinoalkanol precursor compounds.

Example 2

This example illustrates the preparation of the precursor compound 1,1-bis(trifluoromethyl)-2-bis(triphenylphosphino)-ethanol (PO-1H). The compound was made by two different methods.

Method a:

The phosphino alkanol was made according to the procedure in Inorg. Chem. (1985), 24(22), pp. 3680–7. Under nitrogen, 1,1-bis(trifluoromethyl)ethylene oxide (12 g, 0.066 mol) was added dropwise to a pre-cooled (10–15° C.) solution of diphenylphosphine (10 g, 0.053 mol) in dry THF (50 mL). The reaction mixture was stirred at 25° C. for 2 days, after which NMR analysis indicated >90% conversion. The solvent was removed under vacuum and the residual viscous oil was distilled under vacuum to give 8 g of the fraction (b.p. 110–114° C. at 0.05 mm Hg) which crystallized on standing. Both the NMR data and m.p. (59–62° C.) of this material (>95% purity) were consistent with those reported in: Boere, R. T. et al., Inorg. Chem. (1985), 24, 3680. $^1$H NMR (CDCl$_3$, 20° C.), δ: 7.3–7.8 (m, 10H, arom. H); 2.8 (br. s.; 1H, OH); 2.2 (s, 2H, CH$_2$). $^{19}$F NMR (CDCl$_3$, 20° C.), δ: −77.3 (d, J$_{F-P}$=15.5 Hz). $^{31}$P NMR (CDCl$_3$, 20° C.), δ: −24.4 (septet, J$_{P-F}$=15.5 Hz).

Method b:

(i) Preparation of 1,1-bis(trifluoromethyl)-2-bromoethanol, BrCH$_2$C(CF$_3$)$_2$OH. 1,1-bis(trifluoromethyl)oxirane (100 g; 0.55 mol; prepared as described in WO 00/66575, 2000, to DuPont). was added slowly to 100 ml of 47% aqueous HBr placed in a round bottom glass flask equipped with a dry-ice condenser, thermometer, and magnetic stir bar at 30–40° C. The reaction mixture was stirred under reflux for 3 h. At that point the temperature raised to 90° C. After cooling to room temperature, the bottom layer was separated, dried over MgSO$_4$, and distilled to give 104 g (72%) of BrCH$_2$C(CF$_3$)$_2$OH, b.p. 101–103° C. $^1$H NMR (CDCl$_3$): 3.50 (br s, 1H, —OH), 3.70(s, 2H, CH$_2$). $^{19}$F NMR (CDCl$_3$): −75.9 (s). This material was dried over freshly calcined molecular sieves (4 Å) prior to the next step.

(ii) Under nitrogen, to a stirring solution of 1,1-bis (trifluoromethyl)-2-bromoethanol (5.64 g; prepared as described above) in dry ether (110 mL) cooled to −78° C., was added drop-wise 1.6 M n-BuLi in hexanes (Aldrich; 27 mL). After 1 h at −78° C., chlorodiphenylphosphine (Strem; 4.53 g) was added drop-wise, at vigorous stirring, to the resulting solution of the dilithiated derivative. After stirring the mixture for 3 h 20 min at −78° C., it was allowed to warm slowly to room temperature and then stirred at room temperature overnight. The solvents were removed under vacuum. Dichloromethane (10 mL) and trifluoroacetic acid (1.66 mL) were added to the residue, and the mixture was chromatographed on a silica gel column (5×25 cm) with dichloromethane. The product was isolated as an oil which crystallized upon drying under vacuum. The yield of the product as white crystalline solid was 5.3 g (71%). The compound was found identical with the material synthesized according to method a.

1,1-bis(trifluoromethyl)-2-bis(triphenylphosphino)-ethoxide [PO-1]

To make the sodium salt of the ethoxide ligand PO-1, sodium hydride was added to the alcohol in THF. The salt was isolated by removing the volatile components in vacuo.

Example 3

This example illustrates the preparation of the phosphinoalkanol precursor compound Ar$_2$PCH$_2$C(OH)(CF$_3$)$_2$, where Ar=3,5-(CF$_3$)$_2$C$_6$H$_3$ [PO-2H].

Method a:

Under nitrogen, a stirring solution of $(3,5\text{-}(CF_3)_2C_6H_3)_2PH$ (1.50 g; 3.27 mmol; prepared as described in: Casey, C. P. et al., J. Am. Chem. Soc. (1997), 119, 11817) in THF (30 mL) was cooled to −78° C. and treated with a 1.6 M solution of n-BuLi in hexanes (2.06 mL; 3.30 mmol) to produce a deep-purple reaction mixture. To the latter was added, at stirring, 1,1-bis(trifluoromethyl)ethylene oxide (0.59 g; 0.453 mL; 3.27 mmol) and the mixture was allowed to warm to room temperature. After stirring at room temperature overnight, the solution was treated with 0.3 mL of trifluoroacetic acid and evaporated to dryness. Flash-chromatography (silica gel, methylene chloride—hexanes 50:50 by volume) of the residue, followed by vacuum sublimation produced $Ar_2PCH_2C(OH)(CF_3)_2$ (1.52 g; 73%; slightly contaminated with the corresponding phosphine oxide). Anal. Calcd for $C_{20}H_9F_{18}OP$, %: C, 37.6; H, 1.4. Found, %: C, 37.5; H, 1.4. $^1H$ NMR ($CD_2Cl_2$, 20° C.), δ: 8.0 (m, 6H, arom. H); 3.9 (br. s.; 1H, OH); 2.9 (s, 2H, $CH_2$). $^{19}F$ NMR ($CD_2Cl_2$, 20° C.), δ: −63.9 (s, 12F, $(CF_3)_2C_6H_3$); −77.8 (d, $J_{F\text{-}P}$=19.4 Hz, 6F, $(CF_3)_2COH$). $^{31}P$ NMR ($CD_2Cl_2$, 20° C.), δ: −22.1 (septet, $J_{P\text{-}F}$=19.4 Hz).

Method b:

Under nitrogen, to a stirring solution of 1,1-bis(trifluoromethyl)-2-bromoethanol (0.91 g) in dry ether (20 mL) cooled to −78° C., was added drop-wise 1.6 M n-BuLi in hexanes (Aldrich; 4.35 mL). After 1 h at −78° C., $(3,5\text{-}(CF_3)_2C_6H_3)_2PCl$ (1.63 g; prepared as described in: Casalnuovo et al., U.S. Pat. No. 5,175,335) was added drop-wise, at vigorous stirring, to the resulting solution of the dilithiated derivative. After stirring for 2 h at −78° C., the mixture was allowed to warm slowly to room temperature and then stirred at room temperature overnight. The solvents were removed under vacuum. Dichloromethane (5 mL) and trifluoroacetic acid (0.26 mL) were added to the residue. Flash-chromatography (silica gel, dichloromethane) of the mixture produced solid $Ar_2PCH_2C(OH)(CF_3)_2$ (1.32 g; 62%) which was found to be identical to the material synthesized according to method b.

Example 4

This example illustrates the preparation of the phosphinoalkanol precursor compound, $Ar_2PCH_2C(OH)(CF_3)_2$, where Ar=4-$CF_3C_6H_4$ (PO-3H).

Under nitrogen, to a stirring solution of 1,1-bis(trifluoromethyl)-2-bromoethanol (2.28 g) in dry ether (46 mL) cooled to −78° C., was added drop-wise 1.6 M n-BuLi in hexanes (Aldrich; 10.93 mL). After 1 h at −78° C., $(4\text{-}CF_3C_6H_4)_2PCl$ (3.28 g; prepared as described in: Casalnuovo et al., J. Am. Chem. Soc., 1994, 116, 9869) was added drop-wise, at vigorous stirring, to the resulting solution of the dilithiated derivative. After stirring for 2 h at −78° C., the mixture was allowed to warm slowly to room temperature and then stirred at room temperature overnight. The solvents were removed under vacuum. Dichloromethane (7 mL) and trifluoroacetic acid (0.64 mL) were added to the residue. Flash-chromatography (silica gel, dichloromethane) of the mixture, followed by solvent evaporation and vacuum-drying produced $Ar_2PCH_2C(OH)(CF_3)_2$ (3.36 g; 81%) as a slightly yellow oil.). Anal. Calcd for $C_{18}H_{11}F_{12}OP$, %: C, 43.0; H, 2.2. Found, %: C, 42.8; H, 2.2. $^1H$ NMR ($CD_2Cl_2$, 20° C.), δ: 7.7 (m, 8H, arom. H); 3.6 (br. s.; 1H, OH); 2.9 (s, 2H, $CH_2$). $^{19}F$ NMR ($CD_2Cl_2$, 20° C.), δ: −63.5 (s, 6F, $CF_3C_6H_4$); −77.6 (d, $J_{F\text{-}P}$=18.6 Hz, 6F, $(CF_3)_2COH$). $^{31}P$ NMR ($CD_2Cl_2$, 20° C.), δ: −27.1 (septet, $J_{P\text{-}F}$=18.6 Hz).

Example 5

This example illustrates the preparation of the phosphinoalkanol precursor compound, $Ar_2PCH_2C(OH)(CF_3)_2$, where Ar=$C_6F_5$ (PO-4H).

Under nitrogen, to a stirring solution of 1,1-bis(trifluoromethyl)-2-bromoethanol (3.43 g) in dry ether (70 mL) cooled to −78° C., was added drop-wise 1.6 M n-BuLi in hexanes (Aldrich; 16.43 mL). After 30 min at −78° C., $(C_6F_5)_2PCl$ (5.0 g; prepared as described in: RajanBabu et al., J. Org. Chem., 1999, 64, 3429) was added drop-wise, at vigorous stirring, to the resulting solution of the dilithiated derivative. After stirring for 5.5 h at −78° C., the mixture was allowed to warm slowly to room temperature and then stirred at room temperature overnight. The solvents were removed under vacuum. Dichloromethane (10 mL) and trifluoroacetic acid (0.96 mL) were added to the residue. Flash-chromatography (silica gel, dichloromethane) of the mixture, followed by solvent evaporation and vacuum-drying produced $Ar_2PCH_2C(OH)(CF_3)_2$ (1.58 g; 23%) as a white solid. Anal. Calcd for $C_{16}H_3F_{16}OP$, %: C, 35.2; H, 0.55. Found, %: C, 35.1; H, 0.05. $^1H$ NMR ($CD_2Cl_2$, 20° C.), δ: 3.3 (s, 2H, $CH_2$); 3.6 (br. s.; 1H, OH). $^{19}F$ NMR ($CD_2Cl_2$, 20° C.), δ: −77.8 (d, $J_{F\text{-}P}$=20.5 Hz, 6F, $CF_3$); −130.6 (m, 4F, o-$C_6F_5$); −150.0 (t, $J_{F\text{-}F}$=20 Hz; 2F, p-$C_6F_5$); −161.0 (m, 4F, m-$C_6F_5$). $^{31}P$ NMR ($CD_2Cl_2$, 20° C.), δ: −57.6 (m).

Example 6

This example illustrates the formation of dichloro-bridged dinuclear bis-cyclometallated Ir complexes.

The Ir complexes were prepared by the reaction between $IrCl_3.nH_2O$ and the corresponding 2-arylpyridine in aqueous 2-ethoxyethanol. The method is similar to the literatures procedure for 2-phenylpyridine (Sprouse, S.; King, K. A.; Spellane, P. J.; Watts, R. J., J. Am. Chem. Soc., 1984, 106, 6647–53; Garces, F. O.; King, K. A.; Watts, R. J., Inorg. Chem., 1988, 27, 3464–71.). A mixture of $IrCl_3.nH_2O$, a 2-arylpyridine (2.2–2.8 equivalents per Ir), 2-ethoxyethanol (ca. 30 mL per 1 g of $IrCl_3.nH_2O$), and water (ca. 5 mL per 30 mL of 2-ethoxyethanol) was vigorously stirred under reflux ($N_2$) for 4–10 hours. After cooling to room temperature, conc. HCl (3 mL per 1 g $IrCl_3.nH_2O$) was added, and the mixture was stirred for 30 min. The mixture was diluted with water, stirred for 1–2 hours, and filtered. The solid product was washed with water, methanol, and dried under vacuum. The yields ranged from 65 to 99%.

Example 7

This example illustrates the formation of Ir complexes of the invention having the Formula I.

Dicyclometalated Arylpyridine Iridium (III) Mononuclear Complexes Containing Phosphinoalkanol Ligands.

The general procedure was to combine a dichloro-bridged dinuclear bis-cyclometallated Ir complex from Example 6, a phosphinoalkanol compound (1.1–1.5 equivs per Ir), 1,2-dichloroethane (DCE; 3–12 mL), and 10% aqueous NaOH (2–10-fold excess) and stir under reflux (N$_2$) until all solids dissolved and then for additional 0.5–1.5 hours. The products were isolated and purified in air. The organic layer was separated, filtered through a short silica gel plug, and reduced in volume to 0.5–2 mL. Treatment of the residue with hexanes resulted in crystallization (1–3 h) of the desired product which was separated, washed with hexanes, and dried under vacuum. X-ray analysis of three complexes (2-b, 2-g, 2-j, and 2-u) indicated trans arrangement of the nitrogen atoms. $^{31}$P NMR=$^{31}$P-{$^1$H} NMR.

Compound 2-a (Table 2)

A mixture of the dichloro-bridged dinuclear bis-cyclometallated Ir complex made with phenylpyridine compound 1-ab from Example 1 (150 mg), phosphinoalkanol PO-1H from Example 2 (100 mg), DCE (3 mL), and 10% NaOH (1 mL) was vigorously stirred under reflux (N$_2$) for 1 h. The yellow organic layer (blue photoluminescent) was separated and filtered through a short silica plug. The aqueous layer was extracted with dichloromethane and passed through the same plug. The combined organic solutions were reduced in volume to 1–2 mL and treated with hexanes (10 mL; portionwise). The lemon-yellow crystals were separated, washed with hexanes (3×5 mL), and dried under vacuum. Yield: 0.22 g (97%). Anal. Calcd for C$_{40}$H$_{28}$F$_{10}$N$_2$IrOP·C$_2$H$_4$Cl$_2$, %: C, 47.4; H, 3.0; N, 2.6. Found, %: C, 47.5; H, 3.1; N, 2.5. $^1$H NMR (CD$_2$Cl$_2$, 20° C.), δ: 2.5 (s, 3H, CH$_3$); 2.51 (s, 3H, CH$_3$); 3.0 (dd, J$_{H-H}$=16.2 Hz, J$_{H-P}$=9.1 Hz, 1H, CH$_2$); 3.6 (dd, J$_{H-H}$=16.2 Hz, J$_{H-P}$=12.1 Hz, 1H, CH$_2$); 3.8 (s, solvent C$_2$H$_4$Cl$_2$), 5.5 (m, 1H, arom H); 6.1 (m, 1H, arom H); 6.5 (m, 2H, arom H); 6.65 (m, 1H, arom H); 6.7 (m, 3H, arom H); 7.0 (m, 2H, arom H); 7.1 (m, 1H, arom H); 7.4 (m, 3H, arom H); 7.6 (m, 3H, arom H); 8.0 (s, 1H, arom H); 8.2 (s, 1H, arom H); 8.3 (d, 1H, arom H); 8.7 (d, 1H, arom H). $^{19}$F NMR (CD$_2$Cl$_2$, 20° C.), δ: −75.1 (m, 3F, CF$_3$); −78.8 (m, 3F, CF$_3$); −109.2 (m, 1F, arom F); −109.9 (m, 1F, arom F); −110.4 (m, 1F, arom F); −111.0 (m, 1F, arom F). $^{31}$P NMR (CD$_2$Cl$_2$, 20° C.), δ: 10.2 (s).

Compound 2-b (Table 2)

A mixture of the dichloro-bridged dinuclear bis-cyclometallated Ir complex made with phenylpyridine compound 1-ab from Example 1 (200 mg), phosphinoalkanol PO-2H from Example 3 (270 mg), DCE (6 mL), and 10% NaOH (1 mL) was vigorously stirred under reflux (N$_2$) for 25 min. The yellow organic layer (blue photoluminescent) was separated and filtered through a short silica plug. The aqueous layer was extracted with dichloromethane and passed through the same plug. The combined organic solutions were reduced in volume to 1–2 mL and treated with hexanes (10 mL; portionwise). The lemon-yellow crystals were separated, washed with hexanes (3×5 mL), and dried under vacuum. Yield: 0.38 g (97%). Anal. Calcd for C$_{44}$H$_{24}$F$_{22}$N$_2$IrOP, %: C, 42.7; H, 1.9; N, 2.3. Found, %: C, 42.5; H, 1.9; N, 2.3. $^1$H NMR (CD$_2$Cl$_2$, 20° C.), δ: 2.5 (s, 3H, CH$_3$); 2.51 (s, 3H, CH$_3$); 3.1 (dd, J$_{H-H}$=16.2 Hz, J$_{H-P}$=8.3 Hz, 1H, CH$_2$); 3.8 (dd, J$_{H-H}$=16.2 Hz, J$_{H-P}$=12.5 Hz, 1H, CH$_2$); 5.4 (m, 1H, arom H); 6.1 (m, 1H, arom H); 6.6 (m, 2H, arom H); 6.7 (m, 1H, arom H); 6.9 (m, 1H, arom H); 7.25 (m, 2H, arom H); 7.7 (s, 1H, arom H); 8.1 (m, 5H, arom H); 8.25 (m, 1H, arom H); 8.7 (d, 1H, arom H). $^{19}$F NMR (CD$_2$Cl$_2$, 20° C.), δ: −63.8 (s, 6F, arom CF$_3$); −64.1 (s, 6F, arom CF$_3$); −75.0 (m, 3F, HOCCF$_3$); −79.1 (m, 3F, HOCCF$_3$); −107.6 (m, 1F, arom F); −108.1 (m, 1F, arom F); −109.7 (m, 2F, arom F). $^{31}$P NMR (CD$_2$Cl$_2$, 20° C.), δ: 14.6 (s). The structure was confirmed by X-ray analysis.

Compound 2-c (Table 2)

A mixture of the dichloro-bridged dinuclear bis-cyclometallated Ir complex made with phenylpyridine compound 1-ah from Example 1 (200 mg), phosphinoalkanol PO-1H from Example 2 (150 mg), DCE (5 mL), and 10% NaOH (1 mL) was vigorously stirred under reflux (N$_2$) for 0.5 h. The yellow organic layer (blue photoluminescent) was separated and filtered through a short silica plug. The aqueous layer was extracted with dichloromethane and passed through the same plug. The combined organic solutions were reduced in volume to 1–2 mL and treated with hexanes (10 mL; portionwise). The lemon-yellow crystals were separated, washed with hexanes (3×5 mL), and dried under vacuum. Yield: 0.29 g (94%). Anal. Calcd for C$_{38}$H$_{24}$F$_{10}$N$_2$IrOP, %: C, 48.7; H, 2.6; N, 3.0. Found, %: C, 49.1; H, 2.7; N, 2.8. $^1$H NMR (CD$_2$Cl$_2$, 20° C.), δ: 3.05 (dd, J$_{H-H}$=16.2 Hz, J$_{H-P}$=9.1 Hz, 1H, CH$_2$); 3.6 (dd, J$_{H-H}$=16.2 Hz, J$_{H-P}$=12.1 Hz, 1H, CH$_2$); 5.4 (m, 1H, arom H); 6.1 (m, 1H, arom H); 6.5 (m, 2H, arom H); 7.0 (m, 8H, arom H); 7.5 (m, 6H, arom H); 7.7 (t, 1H, arom H); 7.7.8 (t, 1H, arom H); 8.15 (d, 1H, arom H); 8.3 (dd, 1H, arom H); 8.5 (d, 1H, arom H); 8.9 (d, 1H, arom H). $^{19}$F NMR (CD$_2$Cl$_2$, 20° C.), δ: −75.0 (m, 3F, CF$_3$); −78.9 (m, 3F, CF$_3$); −108.6 (m, 1F, arom F); −109.2 (m, 1F, arom F); −110.3 (m, 1F, arom F); −110.9 (m, 1F, arom F). $^{31}$P NMR (CD$_2$Cl$_2$, 20° C.), δ: 10.4(s).

Compound 2-d (Table 2)

A mixture of the dichloro-bridged dinuclear bis-cyclometallated Ir complex made with phenylpyridine compound 1-ah from Example 1 (150 mg), phosphinoalkanol PO-2H from Example 3 (190 mg), DCE (5 mL), and 10% NaOH (1 mL) was vigorously stirred under reflux (N$_2$) for 20 min. The yellow organic layer (blue photoluminescent) was separated and filtered through a short silica plug. The aqueous layer was extracted with dichloromethane and passed through the same plug. The combined organic solutions were reduced in volume to 1–2 mL and treated with hexanes (5 mL). The lemon-yellow needle-shaped crystals were separated, washed with hexanes (3×5 mL), and dried under vacuum. Yield: 0.255 g (85%). Anal. Calcd for C$_{42}$H$_{20}$F$_{22}$N$_2$IrOP, %: C, 41.7; H, 1.7; N, 2.3. Found, %: C, 41.7; H, 1.2; N, 2.4. $^1$H NMR (CD$_2$Cl$_2$, 20° C.), δ: 3.1 (dd, J$_{H-H}$=16.6 Hz, J$_{H-P}$=8.3 Hz, 1H, CH$_2$); 3.8 (dd, J$_{H-H}$=16.6 Hz, J$_{H-P}$=12.4 Hz, 1H, CH$_2$); 5.45 (m, 1H, arom H); 6.15 (m, 1H, arom H); 6.6 (m, 2H, arom H); 6.9 (t, 1H, arom H); 7.0 (t, 1H, arom H); 7.25 (d, 2H, arom H); 7.7 (m, 2H, arom H); 7.9 (t, 1H, arom H); 8.1 (m, 2H, arom H); 8.2 (d, 1H, arom H); 8.25 (d, 1H, arom H); 8.4 (dd, 2H, arom H); 8.9 (d, 1H, arom H). $^{19}$F NMR (CD$_2$Cl$_2$, 20° C.), δ: −63.7 (s, 6F, arom CF$_3$); −64.0 (s, 6F, arom CF$_3$); −75.0 (m, 3F, HOCCF$_3$); −79.1 (m, 3F, HOCCF$_3$); −106.9 (m, 1F, arom F); −107.4 (m, 1F, arom F); −109.5 (m, 2F, arom F). $^{31}$P NMR (CD$_2$Cl$_2$, 20° C.), δ: 14.6 (s).

Compound 2-e (Table 2)

A mixture of the dichloro-bridged dinuclear bis-cyclometallated Ir complex made with phenylpyridine compound 1-ag from Example 1 (110 mg), phosphinoalkanol PO-1H from Example 2 (85 mg), DCE (3 mL), and 10% NaOH (1 mL) was vigorously stirred under reflux (N$_2$) for 0.5 h. The yellow organic layer (blue photoluminescent) was separated and filtered through a short silica plug. The aqueous layer was extracted with dichloromethane and passed through the same plug. The combined organic solutions were reduced in volume to ca. 0.5 mL and treated with hexanes (5 mL; portionwise). The lemon-yellow crystals were separated, washed with hexanes (3×5 mL), and dried under vacuum. Yield: 0.17 g (99%). Anal. Calcd for $C_{40}H_{26}F_{12}N_2IrOP \cdot \frac{1}{2}C_2H_4Cl_2$, %: C, 46.8; H, 2.7; N, 2.7. Found, %: C, 46.4; H, 2.7; N, 2.4. $^1$H NMR ($CD_2Cl_2$, 20° C.), δ: 3.05 (dd, $J_{H-H}$=16.2 Hz, $J_{H-P}$=8.7 Hz, 1H, $CH_2$); 3.65 (dd, $J_{H-H}$=16.2 Hz, $J_{H-P}$=11.7 Hz, 1H, $CH_2$); 3.8 (s, solvent $C_2H_4Cl_2$), 6.1 (m, 1H, arom H); 7.0 (m, 10H, arom H); 7.4 (m, 3H, arom H); 7.5 (m, 2H, arom H); 7.7 (m, 1H, arom H); 7.9 (m, 5H, arom H); 8.5 (d, 1H, arom H); 9.0 (d, 1H, arom H). $^{19}$F NMR ($CD_2Cl_2$, 20° C.), δ: −62.4 (s, 3F, arom $CF_3$); −62.7 (s, 3F, arom $CF_3$); −75.1 (m, 3F, $CF_3$); −79.0 (m, 3F, $CF_3$). $^{31}$P NMR ($CD_2Cl_2$, 20° C.), δ: 10.6 (s).

Compound 2-f (Table 2)

A mixture of the dichloro-bridged dinuclear bis-cyclometallated Ir complex made with phenylpyridine compound 1-ac from Example 1 (350 mg), phosphinoalkanol PO-1H from Example 2 (205 mg), DCE (4 mL), and 10% NaOH (1 mL) was vigorously stirred under reflux ($N_2$) for 30 min. The reaction mixture was extracted with dichloromethane and the combined organic extracts were filtered through a short silica gel plug, then reduced in volume to ca. 1 mL and treated with hexanes (10 mL). After 1 h the pale greenish-yellow crystals (blue-photoluminescent) were separated, washed with hexanes, and dried under vacuum. Yield: 0.44 g (90%). Anal. Calcd for $C_{44}H_{28}F_{18}N_2IrOP$, %: C, 45.3; H, 2.4; N, 2.4. Found, %: C, 45.0; H, 2.2; N, 2.3. $^1$H NMR ($CD_2Cl_2$, 20° C.), δ: 2.35 (s, 3H, $CH_3$); 2.5 (s, 3H, $CH_3$); 2.9 (dd, $J_{H-H}$=16.5 Hz, $J_{H-P}$=10.2 Hz, 1H, $CH_2$); 3.3 (dd, $J_{H-H}$=16.5 Hz, $J_{H-P}$=12.1 Hz, 1H, $CH_2$); 6.5 (d, 1H, arom H); 6.7 (m, 2H, arom H); 6.8 (d, 1H, arom H); 7.0 (m, 2H, arom H); 7.2 (m, 4H, arom H); 7.4 (m, 2H, arom H); 7.5 (m, 1H, arom H); 7.6 (s, 1H, arom H); 7.75 (s, 1H, arom H); 7.9 (d, 2H, arom H); 8.2 (m, 3H, arom H); 8.65 (d, 1H, arom H). $^{19}$F NMR ($CD_2Cl_2$, 20° C.), δ: −58.2 (s, 3F, arom $CF_3$); −59.8 (s, 3F, arom $CF_3$); −62.7 (s, 3F, arom $CF_3$); −63.0 (s, 3F, arom $CF_3$); −73.5 (m, 3F, $HOCCF_3$); −79.2 (m, 3F, $HOCCF_3$). $^{31}$P NMR ($CD_2Cl_2$, 20° C.), δ: 11.4 (s).

Compound 2-g (Table 2)

A mixture of the dichloro-bridged dinuclear bis-cyclometallated Ir complex made with phenylpyridine compound 1-ac from Example 1 (200 mg), phosphinoalkanol PO-2H from Example 3 (190 mg), DCE (5 mL), and 10% NaOH (0.7 mL) was vigorously stirred under reflux ($N_2$) for 15 min. The reaction mixture was extracted with dichloromethane and the combined organic extracts were filtered through a silica gel column, then reduced in volume to ca. 2–3 mL and treated with hexanes (10 mL). The pale-yellow crystals (blue-photoluminescent) were separated, washed with hexanes (3×5 mL), and dried under vacuum. Yield: 0.30 g (87%). Anal. Calcd for $C_{48}H_{24}F_{30}N_2IrOP$, %: C, 40.1; H, 1.7; N, 2.0. Found, %: C, 40.1; H, 1.2; N, 2.1. $^1$H NMR ($CD_2Cl_2$, 20° C.), δ: 2.35 (s, 3H, $CH_3$); 2.55 (s, 3H, $CH_3$); 2.95 (dd, $J_{H-H}$=16.6 Hz, $J_{H-P}$=9.5 Hz, 1H, $CH_2$); 3.6 (dd, $J_{H-H}$=16.6 Hz, $J_{H-P}$=12.5 Hz, 1H, $CH_2$); 6.6 (d, 1H, arom H); 6.8 (d, 1H, arom H); 7.2 (d, 2H, arom H); 7.3 (s, 1H, arom H); 7.6 (m, 3H, arom H); 7.8 (s, 1H, arom H); 7.9 (m, 3H, arom H); 8.1 (s, 2H, arom H); 8.2 (s, 1H, arom H); 8.6 (d, 1H, arom H). $^{19}$F NMR ($CD_2Cl_2$, 20° C.), δ: −58.3 (s, 3F, arom $CF_3$); −60.1 (s, 3F, arom $CF_3$); −63.1 (s, 3F, arom $CF_3$); −63.6 (s, 3F, arom $CF_3$); −63.9 (s, 6F, arom $CF_3$); −64.2 (s, 6F, arom $CF_3$); −73.0 (m, 3F, $HOCCF_3$); −79.7 (m, 3F, $HOCCF_3$). $^{31}$P NMR ($CD_2Cl_2$, 20° C.), δ: 13.7 (s). The structure was confirmed by X-ray analysis.

Compound 2-h (Table 2)

A mixture of the dichloro-bridged dinuclear bis-cyclometallated Ir complex made with phenylpyridine compound 1-ad from Example 1 (430 mg), phosphinoalkanol PO-1H from Example 2 (310 mg), DCE (10 mL), and 10% NaOH (1 mL) was vigorously stirred under reflux ($N_2$) for 1 h. The yellow organic layer (blue photoluminescent) was separated and filtered through a short silica plug. The aqueous layer was extracted with dichloromethane and passed through the same plug. The combined organic solutions were reduced in volume to 1–2 mL and treated with hexanes (10 mL; portionwise). The lemon-yellow crystals were separated, recrystallized from boiling toluene, washed with hexanes (3×5 mL), and dried under vacuum. Yield: 0.45 g (65%). Anal. Calcd for $C_{47}H_{36}F_{10}N_2IrOP$ (1:1 toluene solvate), %: C, 53.4; H, 3.4; N, 2.7. Found, %: C, 53.2; H, 3.1; N, 2.7. $^1$H NMR ($CD_2Cl_2$, 20° C.), δ: 1.9 (s, 3H, $CH_3$); 2.2 (s, 3H, $CH_3$); 2.4 (s, solvent toluene); 3.0 (dd, $J_{H-H}$=16.2 Hz, $J_{H-P}$=9.0 Hz, 1H, $CH_2$); 3.6 (dd, $J_{H-H}$=16.2 Hz, $J_{H-P}$=11.7 Hz, 1H, $CH_2$); 5.5 (m, 1H, arom H); 6.1 (m, 1H, arom H); 6.5 (m, 2H, arom H); 6.7 (m, 2H, arom H); 7.0 (m, 2H, arom H); 7.2 (m, 4H, arom H); 7.5 (m, 8H, arom H); 8.05 (d, 1H, arom H); 8.2 (dd, 1H, arom H); 8.3 (s, 1H, arom H); 8.85 (s, 1H, arom H). $^{19}$F NMR ($CD_2Cl_2$, 20° C.), δ: −75.0 (m, 3F, $CF_3$); −79.0 (m, 3F, $CF_3$); −109.5 (m, 1F, arom F); −110.2 (m, 1F, arom F); −111.4 (m, 1F, arom F); −111.8 (m, 1F, arom F). $^{31}$P NMR ($CD_2Cl_2$, 20° C.), δ: 11.2 (s).

Compound 2-i (Table 2)

A mixture of the dichloro-bridged dinuclear bis-cyclometallated Ir complex made with phenylpyridine compound 1-ad from Example 1 (200 mg), phosphinoalkanol PO-2H from Example 3 (240 mg), DCE (6 mL), and 10% NaOH (1 mL) was vigorously stirred under reflux ($N_2$) for 1 h 10 min. The yellow organic layer (blue photoluminescent) was separated and filtered through a short silica plug. The aqueous layer was extracted with dichloromethane and passed through the same plug. The combined organic solutions were reduced in volume to 2 mL and treated with hexanes (10 mL). After 1 hour, the pale-yellow crystals were separated, washed with hexanes (3×5 mL), and dried under vacuum. Yield: 0.31 g (80%). Anal. Calcd for $C_{44}H_{24}F_{22}N_2IrOP$, %: C, 42.7; H, 1.9; N, 2.3. Found, %: C, 42.5; H, 1.4; N, 2.4. $^1$H NMR ($CD_2Cl_2$, 20° C.), δ: 1.9 (s, 3H, $CH_3$); 2.2 (s, 3H, $CH_3$); 3.1 (dd, $J_{H-H}$=16.2 Hz, $J_{H-P}$=8.7 Hz, 1H, $CH_2$); 3.75 (dd, $J_{H-H}$=16.2 Hz, $J_{H-P}$=12.5 Hz, 1H, $CH_2$); 5.4 (m, 1H, arom H); 6.1 (m, 1H, arom H); 6.6 (m, 2H, arom H); 7.2 (d, 2H, arom H); 7.5 (d, 1H, arom H); 7.7 (m, 2H, arom H); 8.1 (m, 5H, arom H); 8.3 (dd, 1H, arom H); 8.7 (d, 1H, arom H). $^{19}$F NMR ($CD_2Cl_2$, 20° C.), δ: −63.8 (s, 6F, arom $CF_3$); −63.9 (s, 6F, arom $CF_3$); −75.0 (m, 3F, $HOCCF_3$); −79.1 (m, 3F, $HOCCF_3$); −107.9 (m, 1F, arom F); −108.3 (m, 1F, arom F); −110.3 (m, 1 F, arom F); −110.6 (m, 1F, arom F). $^{31}$P NMR ($CD_2Cl_2$, 20° C.), δ: 14.6(s).

Compound 2-i (Table 2)

A mixture of the dichloro-bridged dinuclear bis-cyclometallated Ir complex made with phenylpyridine compound 1-k (340 mg) from Example 1, phosphinoalkanol PO-1H from Example 2 (220 mg), DCE (5 mL), and 10% NaOH (1 mL) was vigorously stirred under reflux ($N_2$) for 20 min. The yellow organic layer (green photoluminescent) was separated and filtered through a short silica plug. The aqueous layer was extracted with dichloromethane and passed through the same plug. The combined organic solutions were reduced in volume to ca. 1 mL and treated with hexanes (10 mL). The yellow oil solidified upon trituration. The solid was recrystallized from dichloromethane-hexanes, washed with hexanes (3×5 mL), and dried under vacuum. Yield: 0.45 g (90%). The structure was confirmed by X-ray analysis (1:1 hydrate with $H_2O$ hydrogen-bonded to the O atom of the complex). $^1H$ NMR ($CD_2Cl_2$, 20° C.), δ: 3.0 (dd, $J_{H-H}$=16.6 Hz, $J_{H-P}$=9.1 Hz, 1H, $CH_2$); 3.6 (dd, $J_{H-H}$=16.2 Hz, $J_{H-P}$=12.1 Hz, 1H, $CH_2$); 3.8 (s, solvent $C_2H_4Cl_2$), 5.5 (m, 1H, arom H); 5.6 (m, 1H, arom H); 6.4 (m, 1H, arom H); 6.7 (m, 4H, arom H); 7.0 (m, 2H, arom H); 7.1 (m, 1H, arom H); 7.4 (m, 3H, arom H); 7.5 (m, 2H, arom H); 7.7 (m, 4H, arom H); 8.0 (m, 2H, arom H); 8.8 (s, 1H, arom H); 9.2 (s, 1H, arom H). $^{19}F$ NMR ($CD_2Cl_2$, 20° C.), δ: −63.3 (br m, 3F, arom $CF_3$); −63.5 (s, 3F, arom $CF_3$); −75.5 (m, 3F, $CF_3$); −78.9 (m, 3F, $CF_3$); −108.0 (m, 1F, arom F); −108.5 (m, 1F, arom F). $^{31}P$ NMR ($CD_2Cl_2$, 20° C.), δ: 12.2 (s).

Compound 2-k (Table 2)

A mixture of the dichloro-bridged dinuclear bis-cyclometallated Ir complex made with phenylpyridine compound 1-ai from Example 1 (300 mg), phosphinoalkanol PO-1H from Example 2 (215 mg), DCE (5 mL), and 10% NaOH (2 mL) was vigorously stirred under reflux ($N_2$) for 2 h. The yellow organic layer (blue photoluminescent) was separated and filtered through a short silica plug. The aqueous layer was extracted with dichloromethane and passed through the same plug. The combined organic solutions were evaporated to dryness and treated with hexanes (10 mL). The yellow oil (blue-photoluminescent) dissolved upon heating the mixture after a few hours at room temperature yellow solid formed. The product was washed with hexanes (3×5 mL), and dried under vacuum. Yield: 0.22 g (50%). Anal. Calcd for $C_{46}H_{40}F_{10}N_2IrOP$, %: C, 52.6; H, 3.8; N, 2.7. Found, %: C, 53.5; H, 3.8; N, 2.8. $^1H$ NMR ($CD_2Cl_2$, 20° C.), δ: 2.5 (s, 3H, $CH_3$); 2.51 (s, 3H, $CH_3$); 3.0 (dd, $J_{H-H}$=16.2 Hz, $J_{H-P}$=9.1 Hz, 1H, $CH_2$); 3.6 (dd, $J_{H-H}$=16.2 Hz, $J_{H-P}$=12.1 Hz, 1H, $CH_2$); 3.8 (s, solvent $C_2H_4Cl_2$), 5.5 (m, 1H, arom H); 6.1 (m, 1H, arom H); 6.5 (m, 2H, arom H); 6.65 (m, 1H, arom H); 6.7 (m, 3H, arom H); 7.0 (m, 2H, arom H); 7.1 (m, 1H, arom H); 7.4 (m, 3H, arom H); 7.6 (m, 3H, arom H); 8.0 (S, 1H, arom H); 8.2 (s, 1H, arom H); 8.3 (d, 1H, arom H); 8.7 (d, 1H, arom H). $^{19}F$ NMR ($CD_2Cl_2$, 20° C.), δ: −75.0 (m, 3F, $CF_3$); −79.0 (m, 3F, $CF_3$); −109.3 (m, 1F, arom F); −110.0 (m, 1F, arom F); −110.7 (m, 1F, arom F); −111.3 (m, 1F, arom F). $^{31}P$ NMR ($CD_2Cl_2$, 20° C.), δ: 10.2 (s).

Compound 2-l (Table 2)

A mixture of the dichloro-bridged dinuclear bis-cyclometallated Ir complex made with phenylpyridine compound 1-aj from Example 1 (217 mg), phosphinoalkanol PO-1H from Example 2 (100 mg), DCE (4 mL), and 10% NaOH (1 mL) was vigorously stirred under reflux ($N_2$) for 10 min. The yellow organic layer (blue-green photoluminescent) was separated and filtered through a short silica plug. The aqueous layer was extracted with dichloromethane and passed through the same plug. The combined organic solutions were evaporated to ca. 1 mL, treated with hexanes (5 mL), and left at room temperature overnight. The yellow crystals (blue-green-photoluminescent) were washed with hexanes (3×2 mL), and dried under vacuum. Yield: 0.195 g (66%). Anal. Calcd for $C_{50}H_{40}F_{18}N_2IrOP$, %: C, 48.0; H, 3.2; N, 2.2. Found, %: C, 47.6; H, 3.0; N, 2.1. $^1H$ NMR ($CD_2Cl_2$, 20° C.), δ: 1.3 (s, 9H, t-Bu); 1.4 (s, 9H, $CH_3$); 2.9 (dd, $J_{H-H}$=16.2 Hz, $J_{H-P}$=10.2 Hz, 1H, $CH_2$); 3.3 (dd, $J_{H-H}$=16.2 Hz, $J_{H-P}$=12.1 Hz, 1H, $CH_2$); 6.6 (dd, 1H, arom H); 6.8 (m, 2H, arom H); 7.0 (m, 3H, arom H); 7.2 (m, 3H, arom H); 7.4 (m, 4H, arom H); 7.6 (s, 1H, arom H); 7.8 (s, 1H, arom H); 8.0 (m, 2H, arom H); 8.2 (s, 1H, arom H); 8.3 (m, 1H, arom H); 8.7 (d, 1H, arom H). 19F NMR ($CD_2Cl_2$, 20° C.), δ: −58.4 (s, 3F, arom $CF_3$); −59.8 (s, 3F, arom $CF_3$); −62.4 (s, 3F, arom $CF_3$); −62.6 (s, 3F, arom $CF_3$); −73.2 (m, 3F, aliph $CF_3$); −79.2 (m, 3F, aliph $CF_3$). $^{31}P$ NMR ($CD_2Cl_2$, 20° C.), δ: 9.8 (s).

Compound 2-m (Table 2)

A mixture of the dichloro-bridged dinuclear bis-cyclometallated Ir complex made with phenylpyridine compound 1-ad from Example 1 (150 mg), phosphinoalkanol PO-3H from Example 4 (140 mg), DCE (5 mL), and 10% NaOH (1 mL) was vigorously stirred under reflux ($N_2$) for 1 h 30 min. The yellow organic layer (blue photoluminescent) was separated and filtered through a short silica plug. The aqueous layer was extracted with dichloromethane and passed through the same plug. The combined organic solutions were reduced in volume to 2 mL and treated with hexanes (10 mL). The pale-yellow crystals were recrystallized from dichloromethane-hexanes, washed with hexanes (3×5 mL), and dried under vacuum. Yield: 0.23 g (88%). Anal. Calcd for $C_{42}H_{26}F_{16}N_2IrOP$, %: C, 45.8; H, 2.4; N, 2.5. Found, %: C, 45.2; H, 2.2; N, 2.4. $^1H$ NMR ($CD_2Cl_2$, 20° C.), δ: 1.9 (s, 3H, $CH_3$); 2.2 (s, 3H, $CH_3$); 3.1 (dd, $J_{H-H}$=16.2 Hz, $J_{H-P}$=9.1 Hz, 1H, $CH_2$); 3.6 (dd, $J_{H-H}$=16.2 Hz, $J_{H-P}$=12.1 Hz, 1H, $CH_2$); 5.5 (m, 1H, arom H); 6.1 (m, 1H, arom H); 6.5 (m, 2H, arom H); 6.9 (m, 2H, arom H); 7.3 (d, 2H, arom H); 7.7 (m, 6H, arom H); 8.0 (m, 1H, arom H); 8.2 (m, 1H, arom H); 8.8 (s, 1H, arom H). $^{19}F$ NMR ($CD_2Cl_2$, 20° C.), δ: −63.9 (s, 3F, arom $CF_3$); −64.0 (s, 3F, arom $CF_3$); −75.0 (m, 3F, $HOCCF_3$); −79.0 (m, 3F, $HOCCF_3$); −108.9 (m, 1F, arom F); −109.2 (m, 1F, arom F); −111.0 (m, 1F, arom F); −111.1 (m, 1F, arom F). $^{31}P$ NMR ($CD_2Cl_2$, 20° C.), δ: 13.1 (s).

Compound 2-n (Table 2)

A mixture of the dichloro-bridged dinuclear bis-cyclometallated Ir complex made with phenylpyridine compound 1-ab from Example 1 (60 mg), phosphinoalkanol PO-3H from Example 4 (60 mg), DCE (3 mL), and 10% NaOH (0.5 mL) was vigorously stirred under reflux ($N_2$) for 30 min. The reaction mixture was extracted with dichloromethane and the combined organic extracts were filtered through a silica gel column, then reduced in volume to ca. 0.5 mL and treated with hexanes (4 mL). The pale-yellow crystals (blue-photoluminescent) were separated, washed with hexanes (3×1 mL), and dried under vacuum. Yield: 0.085 g (82%). Anal. Calcd for $C_{42}H_{26}F_{16}N_2IrOP$, %: C, 45.8; H, 2.4; N, 2.5. Found, %: C, 46.4; H, 2.2; N, 2.3. $^1H$ NMR ($CD_2Cl_2$, 20° C.), δ: 2.35 (s, 3H, $CH_3$); 2.55 (s, 3H, $CH_3$); 2.95 (dd, $J_{H-H}$=16.6 Hz, $J_{H-P}$=9.5 Hz, 1H, $CH_2$); 3.6 (dd, $J_{H-H}$=16.6 Hz, $J_{H-P}$=12.5 Hz, 1H, $CH_2$); 6.6 (d, 1H, arom H); 6.8 (d, 1H, arom H); 7.2 (d, 2H, arom H); 7.3 (s, 1H, arom H); 7.6 (m, 3H, arom H); 7.8 (s, 1H, arom H); 7.9 (m, 3H, arom H); 8.1 (s, 2H, arom H); 8.2 (s, 1H, arom H); 8.6 (d, 1H, arom H). $^{19}$F NMR (CD$_2$Cl$_2$, 20° C.), δ: −63.9 (s, 3F, arom CF$_3$); −64.0 (s, 3F, arom CF$_3$); −75.1 (m, 3F, HOCCF$_3$); −78.8 (m, 3F, HOCCF$_3$). $^{31}$P NMR (CD$_2$Cl$_2$, 20° C.), δ: 12.7 (s).

Compound 2-o (Table 2)

A mixture of the dichloro-bridged dinuclear bis-cyclometallated Ir complex made with phenylpyridine compound 1-al from Example 1 (170 mg), phosphinoalkanol PO-1H from Example 2 (140 mg), DCE (3 mL), and 10% NaOH (1 mL) was vigorously stirred under reflux (N$_2$) for 20 min. The yellow organic layer (green photoluminescent) was separated and filtered through a short silica plug. The aqueous layer was extracted with dichloromethane and passed through the same plug. The combined organic solutions were reduced in volume to ca. 0.5 mL and treated with hexanes (10 mL, portionwise). The yellow crystals were separated, washed with hexanes (3×5 mL), and dried under vacuum. Yield: 0.25 g (92%). Anal. Calcd for C$_{44}$H$_{36}$F$_6$N$_2$IrO$_5$P·½C$_2$H$_4$Cl, %: C, 51.0; H, 3.6; N, 2.6. Found, %: C, 50.7; H, 3.7; N, 2.7. $^1$H NMR (CD$_2$Cl$_2$, 20° C.), δ: 3.0 (dd, J$_{H-H}$=16.2 Hz, J$_{H-P}$=8.7 Hz, 1H, CH$_2$); 3.4 (s, 3H, CH$_3$O); 3.55 (s, 3H, CH$_3$O); 3.6 (dd, J$_{H-H}$=16.2 Hz, J$_{H-P}$=11.3 Hz, 1H, CH$_2$); 3.95 (s, 3H, CH$_3$O); 4.0 (s, 3H, CH$_3$O); 5.05 (m, 1H, arom H); 5.7 (m, 1H, arom H); 6.2 (m, 2H, arom H); 6.6 (m, 1H, arom H); 6.8 (m, 3H, arom H); 6.95 (m, 2H, arom H); 7.05 (m, 1H, arom H); 7.4 (m, 3H, arom H); 7.6 (m, 4H, arom H); 8.4 (d, 1H, arom H); 8.6 (d, 1H, arom H); 8.7 (d, 1H, arom H); 8.9 (d, 1H, arom H). $^{19}$F NMR (CD$_2$Cl$_2$, 20° C.), δ: −75.1 (m, 3F, HOCCF$_3$); −79.0 (m, 3F, HOCCF$_3$). $^{31}$P NMR (CD$_2$Cl$_2$, 20° C.), δ: 8.5 (s).

Compound 2-p (Table 2)

A mixture of the dichloro-bridged dinuclear bis-cyclometallated Ir complex made with phenylpyridine compound 1-al from Example 1 (110 mg), phosphinoalkanol PO-2H from Example 3 (125 mg), DCE (3 mL), and 10% NaOH (1 mL) was vigorously stirred under reflux (N$_2$) for 20 min. The yellow organic layer (bluish-green photoluminescent) was separated and filtered through a short silica plug. The aqueous layer was extracted with dichloromethane and passed through the same plug. The combined organic solutions were reduced in volume to ca. 0.5 mL and treated with hexanes (4 mL). The yellow crystals were separated, washed with hexanes (3×5 mL), and dried under vacuum. Yield: 0.18 g (85%). Anal. Calcd for C$_{46}$H$_{32}$F$_{18}$N$_2$IrO$_5$P, %: C, 43.9; H, 2.6; N, 2.2. Found, %: C, 43.8; H, 2.1; N, 2.4. $^1$H NMR (CD$_2$Cl$_2$, 20° C.), δ: 3.1 (dd, J$_{H-H}$=16.2 Hz, J$_{H-P}$=9.1 Hz, 1H, CH$_2$); 3.4 (s, 3H, CH$_3$O); 3.55 (s, 3H, CH$_3$O); 3.7 (dd, J$_{H-H}$=16.2 Hz, J$_{H-P}$=12.1 Hz, 1H, CH$_2$); 3.95 (s, 3H, CH$_3$O); 4.0 (s, 3H, CH$_3$O); 5.15 (m, 1H, CH$_2$); 3.95 (s, 3H, CH$_3$O); 4.0 (s, 3H, CH$_3$O); 5.15 (m, 1H, arom H); 5.75 (m, 1H, arom H); 6.2 (m, 2H, arom H); 6.7 (m, 1H, arom H); 6.8 (m, 1H, arom H); 7.25 (d, 2H, arom H); 7.5 (t, 1H, arom H); 7.65 (s, 1H, arom H); 7.7 (t, 1H, arom H); 8.0 (s, 1H, arom H); 8.1 (d, 2H, arom H); 8.25 (d, 1H, arom H); 8.45 (d, 1H, arom H); 8.75 (d, 1H, arom H); 8.85 (d, 1H, arom H). $^{19}$F NMR (CD$_2$Cl$_2$, 20° C.), δ: −63.7 (s, 6F, arom CF$_3$); −64.0 (s, 6F, arom CF$_3$); −75.1 (m, 3F, HOCCF$_3$); −78.9 (m, 3F, HOCCF$_3$). $^{31}$P NMR (CD$_2$Cl$_2$, 20° C.), δ: 14.6 (s).

Compound 2-q (Table 2)

A mixture of the dichloro-bridged dinuclear bis-cyclometallated Ir complex made with phenylpyridine compound 1-ae from Example 1 (520 mg), phosphinoalkanol PO-1H from Example 2 (340 mg), DCE (5 mL), and 10% NaOH (1 mL) was vigorously stirred under reflux (N$_2$) for 30 min. The reaction mixture was extracted with toluene and then dichloromethane and the combined organic extracts were filtered through a short silica gel plug, then reduced in volume to ca. 3 mL and treated with hexanes (20 mL). After 1 h the yellow crystals (blue-green photoluminescent) were separated, washed with hexanes, and dried under vacuum. Yield: 0.755 g (92%). Anal. Calcd for C$_{45.5}$H$_{34}$F$_{12}$N$_2$IrOP (crystallized with ½molecule of toluene), %: C, 50.8; H, 3.2; N, 2.6. Found, %: C, 50.8; H, 3.1; N, 2.6. $^1$H NMR (CD$_2$Cl$_2$, 20° C.), δ: 2.55 (s, 3H, CH$_3$); 2.6 (s, 3H, CH$_3$); 3.0 (dd, J$_{H-H}$=16.2 Hz, J$_{H-P}$=8.7 Hz, 1H, CH$_2$); 3.6 (dd, J$_{H-H}$=16.2 Hz, J$_{H-P}$=11.7 Hz, 1H, CH$_2$); 6.1 (m, 1H, arom H); 6.7 (m, 4H, arom H); 6.9 (m, 1H, arom H); 7.0 (m, 2H, arom H); 7.1 (m, 3H, arom H); 7.2 (m, 1H, arom H); 7.5 (m, 3H, arom H); 7.6 (m, 2H, arom H); 7.7 (s, 1H, arom H); 7.8 (s, 1H, arom H); 7.9 (s, 1H, arom H); 7.95 (s, 1H, arom H); 8.3 (d, 1H, arom H); 8.75 (d, 1H, arom H). $^{19}$F NMR (CD$_2$Cl$_2$, 20° C.), δ: −62.2 (s, 3F, arom CF$_3$); −62.8 (s, 3F, arom CF$_3$); −75.2 (m, 3F, HOCCF$_3$); −78.9 (m, 3F, HOCCF$_3$). $^{31}$P NMR (CD$_2$Cl$_2$, 20° C.), δ: 10.3 (s).

Compound 2-r (Table 2)

A mixture of the dichloro-bridged dinuclear bis-cyclometallated Ir complex made with phenylpyridine compound 1-ae from Example 1 (200 mg), phosphinoalkanol PO-2H from Example 3 (230 mg), DCE (5 mL), and 10% NaOH (1 mL) was vigorously stirred under reflux (N$_2$) for 10 min. The reaction mixture was extracted with dichloromethane and the combined organic extracts were filtered through a silica gel column, then reduced in volume to ca. 1–2 mL and treated with hexanes (7 mL). After 3 hours the pale-yellow crystals (blue-photoluminescent) were separated, washed with hexanes (3×3 mL), and dried under vacuum. Yield: 0.34 g (90%). Anal. Calcd for C$_{46}$H$_{26}$F$_{24}$N$_2$IrOP, %: C, 42.4; H, 2.0; N, 2.2. Found, %: C, 42.2; H, 1.4; N, 2.3. $^1$H NMR (CD$_2$Cl$_2$, 20° C.), δ: 2.3 (s, 3H, CH$_3$); 2.6 (s, 3H, CH$_3$); 3.1 (dd, J$_{H-H}$=16.2 Hz, J$_{H-P}$=8.3 Hz, 1H, CH$_2$); 3.8 (dd, J$_{H-H}$=16.2 Hz, J$_{H-P}$=12.1 Hz, 1H, CH$_2$); 6.1 (m, 1H, arom H); 6.7 (m, 2H, arom H); 7.0 (d, 1H, arom H); 7.1 (d, 1H, arom H); 7.2 (m, 3H, arom H); 7.7 (m, 2H, arom H); 7.9 (m, 3H, arom H); 8.1 (m, 4H, arom H); 8.7 (d, 1H, arom H). $^{19}$F NMR (CD$_2$Cl$_2$, 20° C.), δ: −62.9 (s, 3F, arom CF$_3$); −63.0 (s, 3F, arom CF$_3$); −63.6 (s, 3F, arom CF$_3$); −63.9 (s, 3F, arom CF$_3$); −75.1 (m, 3F, HOCCF$_3$); −79.1 (m, 3F, HOCCF$_3$). $^{31}$P NMR (CD$_2$Cl$_2$, 20° C.), δ: 14.6 (s).

Compound 2-s (Table 2)

A mixture of the dichloro-bridged dinuclear bis-cyclometallated Ir complex made with phenylpyridine compound 1-ak from Example 1 (220 mg), phosphinoalkanol PO-1H from Example 2 (140 mg), DCE (4 mL), and 10% NaOH (0.5 mL) was vigorously stirred under reflux (N$_2$) for 25 min. The reaction mixture was extracted with dichloromethane and the combined organic extracts were filtered through a silica gel column, then reduced in volume to ca. 1 mL and treated with hexanes (8 mL). After 1 hour at room temperature and then 30 min at +5° C. the pale-yellow crystals (green-photoluminescent) were separated, washed with hexanes (3×1 mL), and dried under vacuum. Yield: 0.30 g (94%). Anal. Calcd for $C_{42}H_{30}F_{12}N_2IrOP$, %: C, 49.0; H, 2.9; N, 2.7. Found, %: C, 49.0; H, 2.8; N, 2.5. $^1H$ NMR ($CD_2Cl_2$, 20° C.), δ: 2.55 (s, 3H, $CH_3$); 2.6 (s, 3H, $CH_3$); 3.0 (dd, $J_{H-H}$=16.2 Hz, $J_{H-P}$=8.7 Hz, 1H, $CH_2$); 3.6 (dd, $J_{H-H}$=16.2 Hz, $J_{H-P}$=12.1 Hz, 1H, $CH_2$); 6.2 (m, 1H, arom H); 6.7 (m, 3H, arom H); 7.0 (m, 4H, arom H); 7.1 (m, 1H, arom H); 7.4 (m, 7H, arom H); 7.7 (m, 4H, arom H); 8.3 (d, 1H, arom H); 8.8 (d, 1H, arom H). $^{19}F$ NMR ($CD_2Cl_2$, 20° C.), δ: −63.3 (s, 6F, arom $CF_3$); −75.1 (m, 3F, $HOCCF_3$); −79.0 (m, 3F, $HOCCF_3$). $^{31}P$ NMR ($CD_2Cl_2$, 20° C.), δ: 9.0 (s).

Compound 2-t (Table 2)

A mixture of the dichloro-bridged dinuclear bis-cyclometallated Ir complex made with phenylpyridine compound 1-ac from Example 1 (160 mg), phosphinoalkanol PO-4H from Example 5 (120 mg), DCE (4 mL), and 10% NaOH (0.2 mL) was vigorously stirred under reflux ($N_2$) for 10 min. The reaction mixture was extracted with dichloromethane and the combined organic extracts were filtered through a silica gel column, then reduced in volume to ca. 1 mL and treated with hexanes (8 mL). The yellow precipitate was recrystallized from dichlorometane (warm)—hexanes, washed with hexanes (3×1 mL), and dried under vacuum. Yield: 0.222 g (86%). Anal. Calcd for $C_{44}H_{18}F_{28}N_2IrOP$, %: C, 39.3; H, 1.3; N, 2.1. Found, %: C, 39.4; H, 1.2; N, 2.0. $^1H$ NMR ($CD_2Cl_2$, 20° C.), δ: 2.5 (s, 3H, $CH_3$); 2.6 (s, 3H, $CH_3$); 2.7 (dd, $J_{H-H}$=17.0 Hz, $J_{H-P}$=8.7 Hz, 1H, $CH_2$); 4.3 (dd, $J_{H-H}$=17.0 Hz, $J_{H-P}$=ca. 17.0 Hz, 1H, $CH_2$); 6.8 (m, 2H, arom H); 7.6 (s, 1H, arom H); 7.65 (s, 1H, arom H); 7.7 (s, 1H, arom H); 7.9 (s, 1H, arom H); 8.0 (s, 1H, arom H); 8.2 (m, 2H, arom H); 8.7 (d, 1H, arom H). $^{19}F$ NMR ($CD_2Cl_2$, 20° C.), δ: −57.9 (s, 3F, arom $CF_3$); −59.5 (br s, 3F, arom $CF_3$); −62.8 (s, 3F, arom $CF_3$); −63.0 (s, 3F, arom $CF_3$); −74.6 (m, 3F, $HOCCF_3$); −78.7 (m, 3F, $HOCCF_3$); −124.2 (br s, 2F, $C_6F_5$); ca. −128 (very br s, 2F, $C_6F_5$); −144.5 (m, 1F, $C_6F_5$); −147.7 (m, 1F, $C_6F_5$); −157.7 (br s, 2F, $C_6F_5$); −159.8 (br s, 2F, $C_6F_5$). $^{31}P$ NMR ($CD_2Cl_2$, 20° C.), δ: −13.4 (br s).

Compound 2-u (Table 2)

A mixture of the dichloro-bridged dinuclear bis-cyclometallated Ir complex made with phenylpyridine compound 1-ab from Example 1 (100 mg), phosphinoalkanol PO-4H from Example 5 (98 mg), DCE (4 mL), and 10% NaOH (0.2 mL) was vigorously stirred under reflux ($N_2$) for 15 min. The reaction mixture was extracted with dichloromethane and the combined organic extracts were filtered through a silica gel column, then evaporated to dryness. The yellow residue was recrystallized from dichlorometane—hexanes, washed with hexanes (3×1 mL), and dried under vacuum. Yield of the product (1:1 dichloromethane solvate): 0.135 g (70%). Anal. Calcd for $C_{41}H_{20}F_{20}N_2IrOPCl_2$, %: C, 40.0; H, 1.6; N, 2.3. Found, %: C, 40.1; H, 1.5; N, 2.2. $^1H$ NMR ($CD_2Cl_2$, 20° C.), δ: 2.5 (s, 3H, $CH_3$); 2.6 (s, 3H, $CH_3$); 2.7 (dd, $J_{H-H}$=17.0 Hz, $J_{H-P}$=8.7 Hz, 1H, $CH_2$); 4.3 (dd, $J_{H-H}$=17.0 Hz, $J_{H-P}$=ca. 17.0 Hz, 1H, $CH_2$); 6.8 (m, 2H, arom H); 7.6 (s, 1H, arom H); 7.65 (s, 1H, arom H); 7.7 (s, 1H, arom H); 7.9 (s, 1H, arom H); 8.0 (s, 1H, arom H); 8.2 (m, 2H, arom H); 8.7 (d, 1H, arom H). $^{19}F$ NMR ($CD_2Cl_2$, 20° C.), δ: −76.9 (m, 3F, $CF_3$); −78.4 (m, 3F, $CF_3$); −108.0 (m, 1F, arom F); −109.7 (m, 1F, arom F); −109.8 (m, 1F, arom F); −111.8 (m, 1F, arom F); −124.6 (br s, 2F, $C_6F_5$); ca. −129 (very br s, 2F, $C_6F_5$); −145.5 (m, 1F, $C_6F_5$); −148.8 (m, 1F, $C_6F_5$); −158.3 (m, 2F, $C_6F_5$); −160.5 (br s, 2F, $C_6F_5$). $^{31}P$ NMR ($CD_2Cl_2$, 20° C.), δ: −5.3 (br s). The structure/composition was confirmed by X-ray analysis.

Compound 2-v (Table 2)

A mixture of the dichloro-bridged dinuclear bis-cyclometallated Ir complex made with 2-phenylpyridine, prepared as described in Sprouse, S.; King, K. A.; Spellane, P. J.; Watts, R. J., J. Am. Chem. Soc., 1984, 106, 6647–53; Garces, F. O.; King, K. A.; Watts, R. J., Inorg. Chem., 1988, 27, 3464–71 (120 mg), phosphinoalkanol PO-2H from Example 3 (170 mg), DCE (4 mL), and 10% NaOH (1 mL) was vigorously stirred under reflux ($N_2$) for 20 min. The reaction mixture was extracted with dichloromethane and the combined organic extracts were filtered through a silica gel column, then evaporated to 1–2 mL and treated with hexanes (8 mL, portionwise). After 4 hours the yellow precipitate was separated and recrystallized from dichlorometane—hexanes, washed with hexanes (3×1 mL), and dried under vacuum. Yield: 0.22 g (86%). Anal. Calcd for $C_{42}H_{24}F_{18}N_2IrOP$, %: C, 44.3; H, 2.1; N, 2.5. Found, %: C, 43.9; H, 1.6; N, 2.6. $^1H$ NMR ($CD_2Cl_2$, 20° C.), δ: 3.1 (dd, $J_{H-H}$=16.2 Hz, $J_{H-P}$=8.3 Hz, 1H, $CH_2$); 3.8 (dd, $J_{H-H}$=16.2 Hz, $J_{H-P}$=ca. 12.1 Hz, 1H, $CH_2$); 6.0 (m, 1H, arom H); 6.7 (m, 1H, arom H); 6.9 (m, 2H, arom H); 7.0 (m, 4H, arom H); 7.2 (m, 2H, arom H); 7.7 (m, 6H, arom H); 7.9 (m, 2H, arom H); 8.1 (m, 2H, arom H); 8.3 (d, 1H, arom H); 8.9 (d, 1H, arom H). $^{19}F$ NMR ($CD_2Cl_2$, 20° C.), δ: −63.5 (s, 6F, arom $CF_3$); −63.8 (s, 6F, arom $CF_3$); −75.2 (m, 3F, $CF_3COH$); −79.1 (m, 3F, $CF_3COH$). $^{31}P$ NMR ($CD_2Cl_2$, 20° C.), δ: 14.0 (s).

Example 8

This example illustrates the formation of an Ir complex of the invention having the Formula I, in a two-step, one-pot method, directly from $IrCl_3$ (hydrate).

Compound 2-f (Table 2)

A mixture of $IrCl_3$ (hydrate; ca. 54% Ir), arylpyridine 1-ac (12.00 g; 86% purity, contained 14% of 2-chloro-4-methylpyridine starting material), 2-ethoxyethanol (100 mL), and water (20 mL) was stirred under reflux for 2 hours. The solid-free yellow-tan solution was cooled to about 100° C., treated, at stirring, with a solution of NaOH (3.0 g) in water (20 mL) (the mixture turned dark), and then immediately with phosphinoalkanol PO-1H from Example 2 (6.0 g). The mixture turned yellow and a yellow precipitate formed. Water (100 mL) was added, and the mixture was stirred for 5 min at 110° C. (oil bath). The mixture was allowed to cool to room temperature and then kept at ca. 10° C. overnight. The solid was separated by filtration, washed with water, dried on the filter, and dissolved in ca. 400 mL of warm dichloromethane. The solution was filtered through a silica gel column which was then washed with dichloromethane. The combined organic solutions were reduced in volume to ca. 20–30 mL and treated with hexanes (150 mL). After 2 hours the crystalline pale-yellow precipitate was separated, washed with hexanes (4×20 mL), and dried under vacuum. Yield of 2-f: 12.3 g (calculated on Ir). The product was found to be TLC- and spectroscopically pure ($^1H$, $^{19}F$, and $^{31}P$ NMR; see Example 7).

Example 9

This example illustrates the formation of OLEDs using the iridium complexes of the invention.

Thin film OLED devices including a hole transport layer (HT layer), electroluminescent layer (EL layer) and at least one electron transport layer (ET layer) were fabricated by the thermal evaporation technique. An Edward Auto 306 evaporator with oil diffusion pump was used. The base vacuum for all of the thin film deposition was in the range of $10^{-6}$ torr. The deposition chamber was capable of depositing five different films without the need to break up the vacuum.

An indium tin oxide (ITO) coated glass substrate was used, having an ITO layer of about 1000–2000 Å. The substrate was first patterned by etching away the unwanted ITO area with 1N HCl solution, to form a first electrode pattern. Polyimide tape was used as the mask. The patterned ITO substrates were then cleaned ultrasonically in aqueous detergent solution. The substrates were then rinsed with distilled water, followed by isopropanol, and then degreased in toluene vapor for ~3 hours.

The cleaned, patterned ITO substrate was then loaded into the vacuum chamber and the chamber was pumped down to $10^{-6}$ torr. The substrate was then further cleaned using an oxygen plasma for about 5–10 minutes. After cleaning, multiple layers of thin films were then deposited sequentially onto the substrate by thermal evaporation. Finally, patterned metal electrodes of Al were deposited through a mask. The thickness of the film was measured during deposition using a quartz crystal monitor (Sycon STC-200). All film thickness reported in the Examples are nominal, calculated assuming the density of the material deposited to be one. The completed OLED device was then taken out of the vacuum chamber and characterized immediately without encapsulation.

A summary of the device layers and thicknesses is given in Table 5. In all cases the anode was ITO as discussed above, and the cathode was Al having a thickness in the range of 700–760 Å.

TABLE 5

MPMP = bis[4-(N,N-diethylamino)-2-methylphenyl](4-methylphenyl)-methane
DPA = 4,7-diphenyl-1,10-phenanthroline

| Sample | HT layer (Thickness, Å) | EL layer (Thickness, Å) | ET layer (Thickness, Å) |
|---|---|---|---|
| 9-1 | MPMP (538) | Compound 2-a (404) | DPA (408) |
| 9-2 | MPMP (511) | Compound 2-a (411) | DPA (410) |
| 9-3 | MPMP (575) | Compound 2-c (412) | DPA (402) |
| 9-4 | MPMP (511) | Compound 2-d (411) | DPA (411) |
| 9-5 | MPMP (535) | Compound 2-e (423) | DPA (412) |
| 9-6 | MPMP (526) | Compound 2-f (436) | DPA (404) |
| 9-7 | MPMP (505) | Compound 2-g (433) | DPA (408) |
| 9-8 | MPMP (544) | Compound 2-h (424) | DPA (412) |
| 9-9 | MPMP (548) | Compound 2-i (438) | DPA (725) |
| 9-10 | MPMP (510) | Compound 2-k (404) | DPA (414) |
| 9-11 | MPMP (504) | Compound 2-o (422) | DPA (387) |
| 9-12 | MPMP (512) | Compound 2-p (408) | DPA (402) |
| 9-13 | MPMP (546) | Compound 2-q (428) | DPA (411) |
| 9-14 | MPMP (516) | Compound 2-r (462) | DPA (408) |
| 9-15 | MPMP (508) | Compound 2-s (461) | DPA (412) |
| 9-16 | MPMP (514) | Compound 2-v (406) | DPA (407) |

Figure 7:
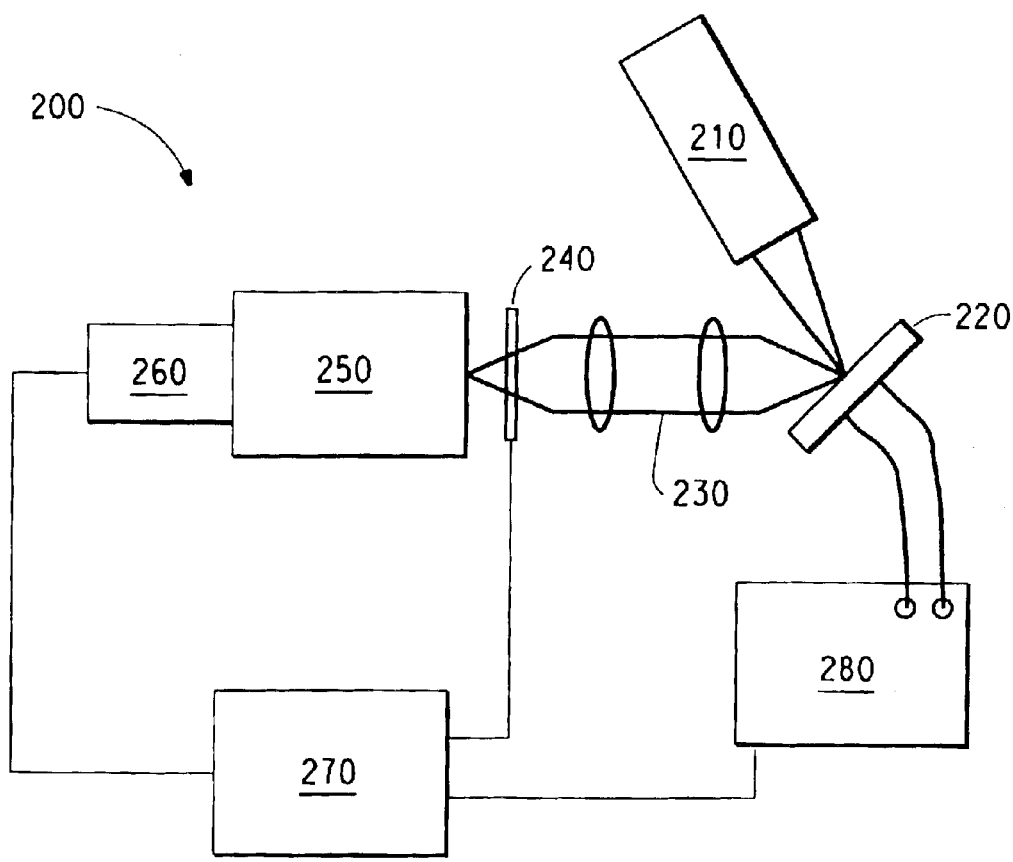
FIG. 7 is a schematic diagram of an LED testing apparatus.

The OLED samples were characterized by measuring their (1) current-voltage (I-V) curves, (2) electroluminescence radiance versus voltage, and (3) electroluminescence spectra versus voltage. The apparatus used, 200, is shown in FIG. 7. The I-V curves of an OLED sample, 220, were measured with a Keithley Source-Measurement Unit Model 237, 280. The electroluminescence radiance (in the unit of $Cd/m^2$) vs. voltage was measured with a Minolta LS-110 luminescence meter, 210, while the voltage was scanned using the Keithley SMU. The electroluminescence spectrum was obtained by collecting light using a pair of lenses, 230, through an electronic shutter, 240, dispersed through a spectrograph, 250, and then measured with a diode array detector, 260. All three measurements were performed at the same time and controlled by a computer, 270. The efficiency of the device at certain voltage is determined by dividing the electroluminescence radiance of the LED by the current density needed to run the device. The unit is in Cd/A. The results are given in Table 6 below:

TABLE 6

Electroluminescent Properties of Iridium Compounds

| Sample | Peak Radiance, Cd/m2 | Peak efficiency, Cd/A | Approximate Peak Wavelengths, nm |
|---|---|---|---|
| 9-1 | 450 at 23 V | 4.5 | 460 and 500 |
| 9-2 | 15 at 20 V | 0.6 | 460 and 490 |
| 9-3 | 450 at 20 V | 2.8 | 465 and 495 |
| 9-4 | 35 at 20 V | 0.4 | 460 and 480 |
| 9-5 | 900 at 22 V | 5.0 | 470 and 510 |
| 9-6 | 450 at 21 V | 12.0 | 470 and 505 |
| 9-7 | 25 at 23 V | 1.0 | 470 and 500 |
| 9-8 | 400 at 22 V | 5.5 | 470 and 500 |
| 9-9 | 190 at 22 V | 1.2 | 465 and 495 |
| 9-10 | 880 at 22 V | 6.0 | 463 and 490 |

TABLE 6-continued

Electroluminescent Properties of Iridium Compounds

| Sample | Peak Radiance, Cd/m2 | Peak efficiency, Cd/A | Approximate Peak Wavelengths, nm |
|---|---|---|---|
| 9-11 | 700 at 21 V | 4.0 | 480 and 510 |
| 9-12 | 120 at 20 V | 0.8 | 478 and 505 |
| 9-13 | 1500 at 22 V | 12.0 | 470 and 500 |
| 9-14 | 250 at 25 V | 1.8 | 468 and 497 |
| 9-15 | 2400 at 22 V | 17.0 | 500 |
| 9-16 | 250 at 22 V | 1.5 | 483 and 506 |

What is claimed is:

1. An organic electronic device comprising an active layer, wherein at least 20% by weight of the active layer comprises at least one compound having Formula I below:

$$IrL^aL^bL' \quad (I)$$

where $L^a$ and $L^b$ are alike or different and each of $L^a$ and $L^b$ has Formula II:

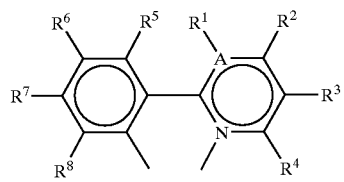

(II)

wherein:

$R^1$ through $R^8$ are independently selected from hydrogen, deuterium, alkyl, alkoxy, halogen, nitro, cyano, fluoro, $C_n(H+F)_{2n+1}$, $OC_n(H+F)_{2n+1}$, and $OCF_2X$, where n is an integer from 1 through 12, and X is H, Cl, or Br, and A is C or N, provided that when A is N, there is no $R^1$; and L' is a bidentate phosphino alkoxide ligand having Formula III:

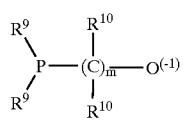

(III)

wherein:

$R^9$ can be the same or different at each occurrence and is selected from $C_6F_5$ and $C_6H_pY_{5-p}$, $R^{10}$ can be the same or different at each occurrence and is selected from H, F, and $C_n(H+F)_{2n+1}$;

Y is $CF_3$;

n is an integer from 1 through 12;

m is 2 or 3;

p is 3 or 4.

2. The device of claim 1 wherein at least one of $R^{10}$ is $CF_3$ and m is 2.

3. The device of claim 1 wherein the phosphino alkoxide ligand is selected from 1,1-bis(trifluoromethyl)-2-(bis(3'5'-ditrifluoromethylphenyl)phosphino)ethoxide; 1,1-bis(trifluoromethyl)-2-(bis(4'-trifluoromethylphenyl)phosphino)ethoxide; and 1,1-bis(trifluoromethyl)-2-(bis(pentafluorophenyl)phosphino)ethoxide.

4. The organic electronic device of claim 1, wherein the compound is selected from compounds 2-a, 2-b, 2-d, 2-g, 2-i, 2-m, 2-n, 2-p, 2-r, 2-t, 2-u, and 2-v, where A is C, $L^a$ is the same as $L^b$, and L' and $R^1$ through $R^8$ are as shown below:

| Compound | L' | $R^1$ | $R^2$ | $R^3$ | $R^4$ | $R^5$ | $R^6$ | $R^7$ | $R^8$ |
|---|---|---|---|---|---|---|---|---|---|
| 2-b | PO-2 | H | CH₃ | H | H | F | H | F | H |
| 2-d | PO-2 | H | H | H | H | F | H | F | H |
| 2-g | PO-2 | H | CH₃ | H | H | H | CF₃ | H | CF₃ |
| 2-i | PO-2 | H | H | CH₃ | H | F | H | F | H |
| 2-m | PO-3 | H | H | CH₃ | H | F | H | F | H |
| 2-n | PO-3 | H | CH₃ | H | H | F | H | F | H |
| 2-p | PO-2 | H | H | H | H | CH₃O | H | CH₃O | H |
| 2-r | PO-2 | H | CH₃ | H | H | H | CF₃ | H | H |
| 2-t | PO-4 | H | CH₃ | H | H | H | CF₃ | H | CF₃ |
| 2-u | PO-4 | H | CH₃ | H | H | F | H | F | H |
| 2-v | PO-2 | H | H | H | H | H | H | H | H | where:

t-Bu is a tertiary butyl group;

PO-2 is 1,1-bis(trifluoromethyl)-2-(bis(3'5'-ditrifluoromethylphenyl)phosphino)ethoxide;

PO-3 is 1,1-bis(trifluoromethyl)-2-(bis(4'-trifluoromethylphenyl)phosphino)ethoxide;

PO-4 is 1,1-bis(trifluoromethyl)-2-(bis(pentafluorophenyl)phosphino)ethoxide.

5. A compound having Formula I below:

$$IrL^aL^bL' \quad (I)$$

where:

$L^a$ and $L^b$ are alike and each of $L^a$ and $L^b$ has Formula II:

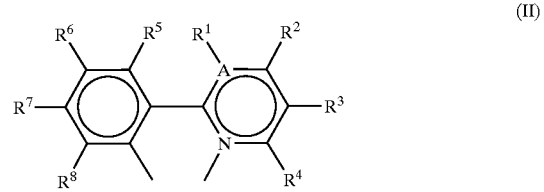

(II)

L' is a bidentate phosphino alkoxide ligand, and wherein the compound is selected from compounds 2-a, 2-b, 2-d, 2-g, 2-i, 2-m, 2-n, 2-p, 2-r, 2-t, 2-u, and 2-v, where A is C, $L^a$ is the same as $L^b$, and L' and $R^1$ through $R^8$ are as shown below:

| Compound | L' | $R^1$ | $R^2$ | $R^3$ | $R^4$ | $R^5$ | $R^6$ | $R^7$ | $R^8$ |
|---|---|---|---|---|---|---|---|---|---|
| 2-b | PO-2 | H | CH₃ | H | H | F | H | F | H |
| 2-d | PO-2 | H | H | H | H | F | H | F | H |
| 2-g | PO-2 | H | CH₃ | H | H | H | CF₃ | H | CF₃ |
| 2-i | PO-2 | H | H | CH₃ | H | F | H | F | H |

-continued

| Compound | L' | R¹ | R² | R³ | R⁴ | R⁵ | R⁶ | R⁷ | R⁸ |
|---|---|---|---|---|---|---|---|---|---|
| 2-m | PO-3 | H | H | CH₃ | H | F | H | F | H |
| 2-n | PO-3 | H | CH₃ | H | H | F | H | F | H |
| 2-p | PO-2 | H | H | H | H | CH₃O | H | CH₃O | H |
| 2-r | PO-2 | H | CH₃ | H | H | H | CF₃ | H | H |
| 2-t | PO-4 | H | CH₃ | H | H | H | CF₃ | H | CF₃ |
| 2-u | PO-4 | H | CH₃ | H | H | F | H | F | H |
| 2-v | PO-2 | H | H | H | H | H | H | H | H | where:

t-Bu is a tertiary butyl group;

PO-2 is 1,1-bis(trifluoromethyl)-2-(bis(3'5'-ditrifluoromethylphenyl)phosphino)ethoxide;

PO-3 is 1,1-bis(trifluoromethyl)-2-(bis(4'-trifluoromethylphenyl)phosphino)ethoxide;

PO-4 is 1,1-bis(trifluoromethyl)-2-(bis(pentafluorophenyl)phosphino)ethoxide.

\* \* \* \* \*